(12) United States Patent
Besson et al.

(10) Patent No.: US 8,771,184 B2
(45) Date of Patent: *Jul. 8, 2014

(54) WIRELESS MEDICAL DIAGNOSIS AND MONITORING EQUIPMENT

(75) Inventors: Marcus Besson, Oberhathing (DE); Gotthart von Czettriz, Munich (DE); Ralph Bax, Munich (DE)

(73) Assignee: Body Science LLC, Plano, TX (US)

(*) Notice: Subject to any disclaimer, the term of this patent is extended or adjusted under 35 U.S.C. 154(b) by 1193 days.

This patent is subject to a terminal disclaimer.

(21) Appl. No.: 11/800,396

(22) Filed: May 4, 2007

(65) Prior Publication Data

US 2007/0208235 A1    Sep. 6, 2007

Related U.S. Application Data

(63) Continuation of application No. 10/396,621, filed on Mar. 24, 2003, now Pat. No. 7,215,991, which is a continuation of application No. 09/882,152, filed on Jun. 15, 2001, now Pat. No. 6,577,893, which is a continuation of application No. 09/379,763, filed on Aug. 24, 1999, now Pat. No. 6,289,238, which is a continuation of application No. 08/985,673, filed on Dec. 5, 1997, now Pat. No. 5,957,854, which is a continuation of application No. 08/605,197, filed as application No. PCT/EP94/02926 on Sep. 2, 1994, now Pat. No. 5,862,803.

(30) Foreign Application Priority Data

Sep. 4, 1993  (DE) .................. P 43 29 898

(51) Int. Cl.
| | |
|---|---|
| A61B 5/00 | (2006.01) |
| A61B 5/04 | (2006.01) |
| A61N 1/39 | (2006.01) |
| H03C 1/62 | (2006.01) |
| H04B 17/00 | (2006.01) |
| H01Q 11/12 | (2006.01) |
| H04B 1/04 | (2006.01) |
| A61B 5/1455 | (2006.01) |

(52) U.S. Cl.
CPC .......... *A61B 5/14552* (2013.01); *A61B 5/6825* (2013.01); *A61B 5/6838* (2013.01); *A61B 2560/0412* (2013.01); *A61B 2560/0219* (2013.01)
USPC ........... 600/300; 600/301; 600/513; 600/519; 600/523; 607/60; 455/115.3; 455/126

(58) Field of Classification Search
None
See application file for complete search history.

(56) References Cited

U.S. PATENT DOCUMENTS

| | | |
|---|---|---|
| 1,151,118 A | 8/1915 | Mylo |
| 2,153,737 A | 4/1939 | Spencer |

(Continued)

FOREIGN PATENT DOCUMENTS

| | | |
|---|---|---|
| CA | 1246148 | 12/1988 |
| DE | 3219558 | 12/1983 |

(Continued)

OTHER PUBLICATIONS

Thorborg, Sten et al. "Mobimed—A Telemedicine System for Mobil Monitoring of Physiological Parameters," SPIE Vo. 1355 Telecommunication for Health Care: Telemetry, Teleradiology, and Telemedicine (1990) pp. 32-35.

(Continued)

*Primary Examiner* — Gary Jackson
*Assistant Examiner* — Shirley Jian
(74) *Attorney, Agent, or Firm* — Martin & Ferraro, LLP

(57) ABSTRACT

A method of medical diagnosis and monitoring using equipment that has wireless electrodes, which are attached to the surface of the skin of the patient. The method comprises collection of data from a patient, converting the data to digital form and transmitting the digital data wirelessly from a patient to a base station located away from the patient where in the wireless transmission between the patient and base station is bi directional.

43 Claims, 6 Drawing Sheets

(56) References Cited

U.S. PATENT DOCUMENTS

| | | |
|---|---|---|
| 2,292,387 A | 8/1942 | Markey et al. |
| 2,864,943 A | 12/1958 | Schultz |
| 2,958,781 A | 11/1960 | Marchal et al. |
| 3,139,086 A | 6/1964 | Botsch et al. |
| 3,199,508 A | 8/1965 | Roth |
| 3,495,584 A | 2/1970 | Schwalm |
| 3,602,215 A | 8/1971 | Parnell |
| 3,603,881 A | 9/1971 | Thornton |
| 3,638,642 A | 2/1972 | Heflin, Sr. |
| 3,639,907 A | 2/1972 | Greatbatch |
| 3,727,190 A | 4/1973 | Vogelman et al. |
| 3,729,708 A | 4/1973 | Wolfer et al. |
| 3,757,778 A | 9/1973 | Graham |
| 3,774,594 A | 11/1973 | Huszar |
| 3,805,796 A | 4/1974 | Terry, Jr. et al. |
| 3,810,102 A | 5/1974 | Parks, III et al. |
| 3,830,228 A | 8/1974 | Foner |
| 3,833,005 A | 9/1974 | Wingrove |
| 3,834,373 A | 9/1974 | Sato |
| 3,900,842 A | 8/1975 | Calabro et al. |
| 3,905,364 A | 9/1975 | Cudahy et al. |
| 3,925,762 A | 12/1975 | Heitlinger et al. |
| 3,943,918 A | 3/1976 | Lewis |
| 3,949,388 A | 4/1976 | Fuller |
| 3,949,397 A | 4/1976 | Wagner et al. |
| 3,970,996 A | 7/1976 | Yasaka et al. |
| 3,986,498 A | 10/1976 | Lewis |
| 4,027,663 A | 6/1977 | Fischler et al. |
| 4,042,906 A | 8/1977 | Ezell |
| 4,051,522 A | 9/1977 | Healy et al. |
| 4,074,228 A | 2/1978 | Jonscher |
| 4,075,632 A | 2/1978 | Baldwin et al. |
| 4,121,573 A | 10/1978 | Crovella et al. |
| 4,124,894 A | 11/1978 | Vick et al. |
| 4,141,351 A | 2/1979 | James et al. |
| 4,142,533 A | 3/1979 | Brownlee et al. |
| 4,150,284 A | 4/1979 | Trenkler et al. |
| 4,156,867 A | 5/1979 | Bench et al. |
| 4,173,221 A | 11/1979 | McLaughlin et al. |
| 4,173,971 A | 11/1979 | Karz |
| 4,186,749 A | 2/1980 | Fryer |
| 4,208,008 A | 6/1980 | Smith |
| 4,216,462 A | 8/1980 | McGrath et al. |
| 4,233,241 A | 11/1980 | Kalopissis et al. |
| 4,233,985 A | 11/1980 | Hartlaub et al. |
| 4,236,524 A | 12/1980 | Powell et al. |
| 4,237,900 A | 12/1980 | Schulman et al. |
| 4,250,884 A | 2/1981 | Hartlaub et al. |
| 4,253,466 A | 3/1981 | Hartlaub et al. |
| 4,257,423 A | 3/1981 | McDonald et al. |
| 4,260,951 A | 4/1981 | Lewyn |
| 4,262,632 A | 4/1981 | Hanton et al. |
| 4,273,132 A | 6/1981 | Hartlaub et al. |
| 4,273,133 A | 6/1981 | Hartlaub et al. |
| 4,276,883 A | 7/1981 | McDonald et al. |
| 4,281,664 A | 8/1981 | Duggan |
| 4,321,933 A | 3/1982 | Baessler |
| 4,353,372 A | 10/1982 | Ayer |
| 4,379,459 A | 4/1983 | Stein |
| 4,396,906 A | 8/1983 | Weaver |
| 4,409,594 A | 10/1983 | Graziani |
| 4,411,267 A | 10/1983 | Heyman |
| 4,416,283 A | 11/1983 | Slocum |
| 4,425,921 A | 1/1984 | Fujisaki et al. |
| 4,441,498 A | 4/1984 | Nordling |
| 4,449,536 A | 5/1984 | Weaver |
| 4,467,807 A | 8/1984 | Bornzin |
| 4,471,786 A | 9/1984 | Inagaki et al. |
| 4,475,208 A | 10/1984 | Ricketts |
| 4,476,868 A | 10/1984 | Thompson |
| 4,510,495 A | 4/1985 | Sigrimis et al. |
| 4,521,918 A | 6/1985 | Challen |
| 4,531,523 A | 7/1985 | Anderson |
| 4,531,526 A | 7/1985 | Genest |
| 4,537,200 A | 8/1985 | Widrow |
| 4,556,061 A | 12/1985 | Barreras et al. |
| 4,556,063 A | 12/1985 | Thompson et al. |
| 4,562,840 A | 1/1986 | Batina et al. |
| 4,562,841 A | 1/1986 | Brockway et al. |
| 4,573,026 A | 2/1986 | Curtis et al. |
| 4,577,639 A | 3/1986 | Simon et al. |
| 4,583,548 A | 4/1986 | Schmid |
| 4,583,549 A | 4/1986 | Manoli |
| 4,585,004 A | 4/1986 | Brownlee |
| 4,586,508 A | 5/1986 | Batina et al. |
| 4,598,281 A | 7/1986 | Maas |
| 4,599,723 A | 7/1986 | Eck |
| 4,601,043 A | 7/1986 | Hardt et al. |
| 4,606,352 A | 8/1986 | Geddes et al. |
| 4,608,994 A | 9/1986 | Ozawa et al. |
| 4,618,861 A | 10/1986 | Gettens et al. |
| 4,625,733 A | 12/1986 | Saynajakangas |
| 4,638,313 A | 1/1987 | Sherwood, Jr. et al. |
| RE32,361 E | 2/1987 | Duggan |
| 4,653,068 A | 3/1987 | Kadin |
| 4,681,111 A | 7/1987 | Silvian |
| 4,681,118 A | 7/1987 | Asai et al. |
| 4,702,253 A | 10/1987 | Nappholz et al. |
| 4,709,704 A | 12/1987 | Lukasiewicz |
| 4,724,435 A | 2/1988 | Moses et al. |
| 4,747,413 A | 5/1988 | Bloch |
| 4,750,495 A | 6/1988 | Brumwell et al. |
| 4,754,483 A | 6/1988 | Weaver |
| 4,757,825 A | 7/1988 | Diamond |
| 4,783,844 A | 11/1988 | Higashiyama et al. |
| 4,784,162 A | 11/1988 | Ricks et al. |
| 4,791,933 A | 12/1988 | Asai et al. |
| 4,794,532 A | 12/1988 | Leckband et al. |
| 4,799,059 A | 1/1989 | Grindahl et al. |
| 4,802,222 A | 1/1989 | Weaver |
| 4,803,625 A | 2/1989 | Fu et al. |
| 4,805,631 A | 2/1989 | Foi du Maroc, II |
| 4,807,629 A | 2/1989 | Baudino et al. |
| 4,835,372 A | 5/1989 | Gombrich et al. |
| 4,839,806 A | 6/1989 | Goldfischer et al. |
| 4,850,009 A | 7/1989 | Zook et al. |
| 4,857,893 A | 8/1989 | Carroll |
| 4,860,759 A | 8/1989 | Kahn et al. |
| 4,865,044 A | 9/1989 | Wallace et al. |
| 4,883,064 A | 11/1989 | Olson et al. |
| 4,889,131 A | 12/1989 | Salem et al. |
| 4,889,132 A | 12/1989 | Hutcheson et al. |
| 4,907,248 A | 3/1990 | Bretl |
| 4,907,845 A | 3/1990 | Wood |
| 4,909,260 A | 3/1990 | Salem et al. |
| 4,916,441 A | 4/1990 | Gombrich |
| 4,928,187 A | 5/1990 | Rees |
| 4,939,731 A | 7/1990 | Reed et al. |
| 4,955,075 A | 9/1990 | Anderson |
| 4,957,109 A | 9/1990 | Groeger et al. |
| 4,958,645 A | 9/1990 | Cadell et al. |
| 4,966,154 A | 10/1990 | Cooper et al. |
| 4,974,607 A | 12/1990 | Miwa |
| 4,979,506 A | 12/1990 | Silvian |
| 4,981,141 A | 1/1991 | Segalowitz |
| 5,002,060 A | 3/1991 | Nedivi |
| 5,002,064 A | 3/1991 | Allain et al. |
| 5,012,411 A | 4/1991 | Poliscastro et al. |
| 5,024,221 A | 6/1991 | Morgan |
| 5,025,452 A | 6/1991 | Sohner et al. |
| 5,025,808 A | 6/1991 | Hafner |
| 5,036,462 A | 7/1991 | Kaufman et al. |
| 5,036,869 A | 8/1991 | Inahara |
| 5,042,498 A | 8/1991 | Dukes |
| 5,051,799 A | 9/1991 | Paul et al. |
| 5,052,388 A | 10/1991 | Sivula et al. |
| 5,072,383 A | 12/1991 | Brimm et al. |
| 5,077,753 A | 12/1991 | Grau |
| 5,078,134 A | 1/1992 | Heilman et al. |
| 5,080,096 A | 1/1992 | Hooper et al. |
| 5,085,224 A | 2/1992 | Galen et al. |
| 5,086,776 A | 2/1992 | Fowler, Jr. et al. |
| 5,091,945 A | 2/1992 | Kleijn |
| 5,101,825 A | 4/1992 | Gravenstein et al. |

(56) References Cited

U.S. PATENT DOCUMENTS

| | | | |
|---|---|---|---|
| 5,107,833 A | | 4/1992 | Barsness |
| 5,109,845 A | | 5/1992 | Yuuchi et al. |
| 5,113,869 A | | 5/1992 | Nappholz et al. |
| 5,127,404 A | | 7/1992 | Wyborny et al. |
| 5,131,399 A | | 7/1992 | Sciarra |
| 5,137,022 A | | 8/1992 | Henry |
| 5,153,584 A | | 10/1992 | Engira |
| 5,157,604 A | | 10/1992 | Axford et al. |
| 5,161,154 A | | 11/1992 | Diaz et al. |
| 5,164,879 A | | 11/1992 | Danowski et al. |
| 5,168,874 A | | 12/1992 | Segalowitz |
| 5,171,977 A | | 12/1992 | Morrison |
| 5,177,765 A | | 1/1993 | Holland et al. |
| 5,177,766 A | | 1/1993 | Holland et al. |
| 5,179,569 A | | 1/1993 | Sawyer |
| 5,179,571 A | | 1/1993 | Schilling |
| 5,181,519 A | | 1/1993 | Bible |
| 5,192,949 A | | 3/1993 | Suzuki et al. |
| 5,205,294 A | | 4/1993 | Flach et al. |
| 5,212,476 A | | 5/1993 | Maloney |
| 5,212,715 A | | 5/1993 | Pickert et al. |
| 5,222,020 A | | 6/1993 | Takeda |
| 5,224,485 A | | 7/1993 | Powers et al. |
| 5,226,413 A | | 7/1993 | Bennett et al. |
| 5,226,431 A | | 7/1993 | Bible et al. |
| 5,238,001 A | | 8/1993 | Gallant et al. |
| 5,243,979 A | | 9/1993 | Stein et al. |
| 5,257,397 A | | 10/1993 | Barzegar et al. |
| 5,262,944 A | | 11/1993 | Weisner et al. |
| 5,270,811 A | | 12/1993 | Ishibashi et al. |
| 5,272,477 A | | 12/1993 | Tashima et al. |
| 5,292,343 A | | 3/1994 | Blanchette et al. |
| 5,305,202 A | | 4/1994 | Gallant et al. |
| 5,305,353 A | | 4/1994 | Weerackody |
| 5,307,372 A | | 4/1994 | Sawyer et al. |
| 5,307,817 A | | 5/1994 | Guggenbuhl et al. |
| 5,307,818 A | | 5/1994 | Segalowitz |
| 5,309,920 A | | 5/1994 | Gallant et al. |
| 5,314,450 A | | 5/1994 | Thompson |
| 5,319,363 A | | 6/1994 | Welch et al. |
| 5,327,478 A | | 7/1994 | Lebowitz |
| 5,335,664 A | | 8/1994 | Nagashima |
| 5,339,824 A | | 8/1994 | Engira |
| 5,342,408 A | | 8/1994 | deCoriolis et al. |
| 5,343,869 A | | 9/1994 | Pross et al. |
| 5,344,431 A | | 9/1994 | Merritt et al. |
| 5,348,008 A | | 9/1994 | Bornn et al. |
| 5,350,411 A | | 9/1994 | Ryan et al. |
| 5,353,791 A | | 10/1994 | Tamura et al. |
| 5,353,793 A | | 10/1994 | Bornn |
| 5,354,319 A | | 10/1994 | Wyborny et al. |
| 5,359,641 A | | 10/1994 | Schull et al. |
| 5,365,530 A | | 11/1994 | Yoshida |
| 5,372,607 A | * | 12/1994 | Stone et al. ............ 607/30 |
| 5,375,604 A | | 12/1994 | Kelly et al. |
| 5,377,222 A | | 12/1994 | Sanderford, Jr. |
| 5,381,798 A | | 1/1995 | Burrows |
| 5,381,804 A | | 1/1995 | Shambroom |
| 5,388,586 A | | 2/1995 | Lee et al. |
| 5,390,238 A | | 2/1995 | Kirk et al. |
| 5,392,771 A | | 2/1995 | Mock et al. |
| 5,394,879 A | | 3/1995 | Gorman |
| 5,394,882 A | | 3/1995 | Mawhinney |
| 5,400,794 A | | 3/1995 | Gorman |
| 5,416,695 A | | 5/1995 | Stutman et al. |
| 5,417,222 A | | 5/1995 | Dempsey et al. |
| 5,425,051 A | | 6/1995 | Mahany |
| 5,425,372 A | | 6/1995 | Takeda |
| 5,434,396 A | | 7/1995 | Owen et al. |
| 5,438,329 A | | 8/1995 | Gastouniotis et al. |
| 5,438,607 A | | 8/1995 | Przygoda, Jr. et al. |
| 5,441,047 A | | 8/1995 | David et al. |
| 5,444,719 A | | 8/1995 | Cox et al. |
| 5,450,616 A | * | 9/1995 | Rom ............ 455/69 |
| 5,458,122 A | | 10/1995 | Hethuin |
| 5,458,123 A | | 10/1995 | Unger |
| 5,458,124 A | | 10/1995 | Stanko et al. |
| 5,464,021 A | | 11/1995 | Birnbaum |
| 5,485,848 A | | 1/1996 | Jackson et al. |
| 5,487,060 A | | 1/1996 | Rosen et al. |
| 5,487,069 A | | 1/1996 | O'Sullivan et al. |
| 5,491,474 A | | 2/1996 | Suni et al. |
| 5,502,726 A | | 3/1996 | Fischer |
| 5,507,035 A | | 4/1996 | Bantz et al. |
| 5,511,533 A | | 4/1996 | Waller |
| 5,522,396 A | | 6/1996 | Langer et al. |
| 5,524,637 A | | 6/1996 | Erickson |
| 5,537,421 A | | 7/1996 | Dujari et al. |
| 5,538,007 A | | 7/1996 | Gorman |
| 5,544,649 A | | 8/1996 | David et al. |
| 5,544,661 A | | 8/1996 | Davis et al. |
| 5,546,950 A | | 8/1996 | Schoeckert et al. |
| 5,549,113 A | | 8/1996 | Halleck et al. |
| 5,558,638 A | | 9/1996 | Evers et al. |
| 5,564,429 A | | 10/1996 | Bornn et al. |
| 5,568,814 A | | 10/1996 | Gallant et al. |
| 5,576,952 A | | 11/1996 | Stutman et al. |
| 5,579,001 A | | 11/1996 | Dempsey et al. |
| 5,579,378 A | | 11/1996 | Arlinghaus, Jr. |
| 5,579,775 A | | 12/1996 | Dempsey et al. |
| 5,579,781 A | | 12/1996 | Cooke |
| 5,582,180 A | | 12/1996 | Manset et al. |
| 5,586,552 A | | 12/1996 | Sakai |
| 5,600,663 A | * | 2/1997 | Ayanoglu et al. ............ 714/774 |
| 5,601,615 A | * | 2/1997 | Markowitz et al. ............ 607/28 |
| 5,617,871 A | | 4/1997 | Burrows |
| 5,628,324 A | | 5/1997 | Sarbach |
| 5,628,326 A | | 5/1997 | Arand et al. |
| 5,634,468 A | | 6/1997 | Platt et al. |
| 5,640,953 A | | 6/1997 | Bishop et al. |
| 5,646,701 A | | 7/1997 | Duckworth et al. |
| 5,664,270 A | | 9/1997 | Bell et al. |
| 5,669,391 A | | 9/1997 | Williams |
| 5,678,545 A | | 10/1997 | Stratbucker |
| 5,678,562 A | | 10/1997 | Sellers |
| 5,685,303 A | | 11/1997 | Rollman et al. |
| 5,694,940 A | | 12/1997 | Unger et al. |
| 5,699,365 A | | 12/1997 | Klayman et al. |
| 5,704,351 A | | 1/1998 | Mortara et al. |
| 5,718,234 A | | 2/1998 | Warden et al. |
| 5,720,771 A | | 2/1998 | Snell |
| 5,724,985 A | | 3/1998 | Snell |
| 5,738,102 A | | 4/1998 | Lemelson |
| 5,748,103 A | | 5/1998 | Flach et al. |
| 5,752,976 A | | 5/1998 | Duffin et al. |
| 5,752,977 A | | 5/1998 | Grevious et al. |
| 5,755,230 A | | 5/1998 | Schmidt et al. |
| 5,759,199 A | | 6/1998 | Snell et al. |
| 5,767,791 A | | 6/1998 | Stoop et al. |
| 5,779,630 A | | 7/1998 | Fein et al. |
| 5,782,890 A | | 7/1998 | Wahlstrand et al. |
| 5,788,633 A | | 8/1998 | Mahoney |
| 5,800,204 A | | 9/1998 | Niitsu |
| 5,813,404 A | | 9/1998 | Devlin et al. |
| 5,819,740 A | | 10/1998 | Muhlenberg |
| 5,820,567 A | | 10/1998 | Mackie |
| 5,827,179 A | | 10/1998 | Lichter et al. |
| 5,862,803 A | | 1/1999 | Besson et al. |
| 5,865,733 A | | 2/1999 | Malinouskas et al. |
| 5,868,671 A | | 2/1999 | Mahoney |
| 5,871,451 A | | 2/1999 | Unger et al. |
| 5,873,369 A | | 2/1999 | Laniado et al. |
| 5,882,300 A | | 3/1999 | Malinouskas et al. |
| 5,889,474 A | | 3/1999 | LaDue |
| 5,899,928 A | | 5/1999 | Sholder et al. |
| 5,899,931 A | | 5/1999 | Deschamp et al. |
| 5,907,291 A | | 5/1999 | Chen et al. |
| 5,913,827 A | | 6/1999 | Gorman |
| 5,917,414 A | | 6/1999 | Oppelt et al. |
| 5,919,141 A | | 7/1999 | Money et al. |
| 5,919,214 A | | 7/1999 | Ciciarelli et al. |
| 5,929,782 A | | 7/1999 | Stark et al. |
| 5,930,295 A | | 7/1999 | Isley, Jr. et al. |
| 5,931,791 A | | 8/1999 | Saltzstein et al. |

(56) References Cited

U.S. PATENT DOCUMENTS

| | | |
|---|---|---|
| 5,935,078 A | 8/1999 | Feierbach |
| 5,938,597 A | 8/1999 | Stratbucker |
| 5,944,659 A | 8/1999 | Flach et al. |
| 5,949,352 A | 9/1999 | Ferrari |
| 5,954,536 A | 9/1999 | Fuerst et al. |
| 5,954,539 A | 9/1999 | Hornung |
| 5,954,719 A | 9/1999 | Chen et al. |
| 5,957,854 A | 9/1999 | Besson et al. |
| 5,959,529 A | 9/1999 | Kail, IV |
| 5,960,119 A | 9/1999 | Echigo et al. |
| 5,961,448 A | 10/1999 | Swenson et al. |
| 5,963,650 A | 10/1999 | Simionescu et al. |
| 5,964,701 A | 10/1999 | Asada et al. |
| 5,966,692 A | 10/1999 | Langer et al. |
| 5,970,105 A | 10/1999 | Dacus |
| 5,995,861 A | 11/1999 | Price |
| 5,999,857 A | 12/1999 | Weijand et al. |
| 6,006,125 A | 12/1999 | Kelly et al. |
| 6,009,350 A | 12/1999 | Renken |
| 6,010,359 A | 1/2000 | Etters et al. |
| 6,024,699 A | 2/2000 | Surwit |
| 6,027,363 A | 2/2000 | Watt et al. |
| 6,032,065 A | 2/2000 | Brown |
| 6,039,600 A | 3/2000 | Etters et al. |
| 6,047,201 A | 4/2000 | Jackson, III |
| 6,053,887 A | 4/2000 | Levitas et al. |
| 6,057,758 A | 5/2000 | Dempsey et al. |
| 6,066,093 A | 5/2000 | Kelly et al. |
| 6,073,046 A | 6/2000 | Patel et al. |
| 6,074,345 A | 6/2000 | Van Oostrom et al. |
| 6,076,003 A | 6/2000 | Rogel |
| 6,077,124 A | 6/2000 | Etters et al. |
| 6,083,248 A | 7/2000 | Thompson |
| 6,086,412 A | 7/2000 | Watt et al. |
| 6,093,146 A | 7/2000 | Filangeri |
| 6,102,856 A | 8/2000 | Groff |
| 6,117,076 A | 9/2000 | Cassidy |
| 6,141,575 A | 10/2000 | Price |
| 6,141,788 A | 10/2000 | Rosenberg et al. |
| 6,146,190 A | 11/2000 | Fuerst et al. |
| 6,147,618 A | 11/2000 | Halleck et al. |
| 6,149,602 A | 11/2000 | Arcelus |
| 6,154,676 A | 11/2000 | Levine |
| 6,163,276 A | 12/2000 | Irving et al. |
| 6,181,734 B1 | 1/2001 | Palermo |
| 6,184,797 B1 | 2/2001 | Stark |
| 6,198,394 B1 | 3/2001 | Jacobsen et al. |
| 6,206,837 B1 | 3/2001 | Brugnoli |
| 6,208,889 B1 | 3/2001 | Gorman |
| 6,213,942 B1 | 4/2001 | Flach et al. |
| 6,225,901 B1 | 5/2001 | Kail, IV |
| 6,236,874 B1 | 5/2001 | Devlin et al. |
| 6,237,105 B1 | 5/2001 | Walsh et al. |
| 6,238,338 B1 | 5/2001 | DeLuca et al. |
| 6,244,890 B1 | 6/2001 | Fuerst et al. |
| 6,252,883 B1 | 6/2001 | Schweickart |
| 6,267,723 B1 | 7/2001 | Matsumura et al. |
| 6,287,252 B1 | 9/2001 | Lugo |
| 6,289,238 B1 | 9/2001 | Besson et al. |
| 6,295,466 B1 | 9/2001 | Ishikara et al. |
| 6,304,774 B1 | 10/2001 | Gorman |
| 6,319,200 B1 | 11/2001 | Lai et al. |
| 6,332,094 B1 | 12/2001 | Gorman |
| 6,348,008 B1 | 2/2002 | Bertoniere |
| 6,364,834 B1 | 4/2002 | Reuss et al. |
| 6,389,308 B1 | 5/2002 | Shusterman |
| 6,416,471 B1 | 7/2002 | Kumar et al. |
| 6,440,067 B1 | 8/2002 | DeLuca et al. |
| 6,441,747 B1 | 8/2002 | Khair |
| 6,443,891 B1 | 9/2002 | Grevious |
| 6,450,953 B1 | 9/2002 | Place et al. |
| 6,480,733 B1 | 11/2002 | Turcott |
| 6,496,705 B1 | 12/2002 | Ng et al. |
| 6,544,173 B2 | 4/2003 | West et al. |
| 6,544,174 B2 | 4/2003 | West et al. |
| 6,577,893 B1 | 6/2003 | Besson |
| 6,611,705 B2 | 8/2003 | Hopman et al. |
| 6,616,606 B1 | 9/2003 | Petersen et al. |
| 6,658,276 B2 | 12/2003 | Kianl |
| 6,804,558 B2 | 10/2004 | Haller et al. |
| 7,215,991 B2 | 5/2007 | Besson |
| 7,260,159 B2 | 8/2007 | Lee et al. |
| 2002/0038094 A1 | 3/2002 | Gorman |

FOREIGN PATENT DOCUMENTS

| | | |
|---|---|---|
| DE | 43 29 898 | 4/1995 |
| EP | 0212278 | 3/1987 |
| EP | 0262205 | 10/1988 |
| EP | 0354251 | 2/1990 |
| EP | 0476242 | 3/1992 |
| EP | 0553372 | 8/1993 |
| EP | 0610030 | 8/1994 |
| EP | 0779057 | 6/1997 |
| GB | 2 003 276 | 3/1979 |
| GB | 2003276 | 3/1979 |
| GB | 1 543 441 | 4/1979 |
| GB | 1543441 | 4/1979 |
| GB | 2 259 772 | 3/1993 |
| GB | 2259772 | 3/1993 |
| GB | 2271691 | 4/1994 |
| WO | WO 87/06113 | 10/1987 |
| WO | WO 88/02237 | 4/1988 |
| WO | WO 90/08501 | 8/1990 |
| WO | WO 91/18550 | 12/1991 |
| WO | WO 92/07505 | 5/1992 |
| WO | WO 94/01039 | 1/1994 |
| WO | WO 94/02926 | 2/1994 |
| WO | WO 95/07048 | 3/1995 |
| WO | WO 97/49077 | 12/1997 |
| WO | WO 98/00056 | 1/1998 |
| WO | WO 00/62667 | 10/2000 |
| WO | 02/062205 | 8/2002 |

OTHER PUBLICATIONS

Carr, Joseph J. et al., "Introduction to Biomedical Equipment Technology," (610 pages) ($22^{nd}$ ed. 1993).
Paulos, John J. et al. "Custom Integrated Circuits for Biomedical Applications" (4 pages).
"Transmission Networks" pp. 33-34.
Akyildiz, I.F. et al., "Wireless Sensor Networks: A Survey," 38 Computer Networks pp. 393-422 (2002).
Bachmann, K. et al., "Radiotelemetry of Direct Bloodpressure Measurements in Aorta, Pulmonary Artery and Heart," Biotelemetry International Symposium, Nijmegen, Netherlands pp. 183-95 (May 5-8, 1971).
"Biotelementry International Symposium" (eds. Kimmich H.P. et al.) (1972).
Bryan, John "Data Over Cellular—Enhanced Throughput Celllular Makes you Forget That Your Data is Riding on an Analog Connection," 19 BYTE No. 9 (Sep. 1, 1994).
CCITT—The International Telegraph and Telephone Consultative Committee, "Data Communication Over the Telephone Network—A Duplex Modem Operating at Data Signalling Rates of Up to 14 400 bit/s for Use on the General Switched Telephone Network and on Leased Point-to-Point 2-Wire Telephone-Type Circuits—Recommendation V.32 bis," pp. 1-22 (1991).
Chan, J.M. Ng. E. et al., "A Multimedia Conferencing System for Co-Operative Medical Diagnosis," Sixth Annual IEEE Symposium on Computer-Based Medical Systems pp. 94-99 (copyright 1993).
Gao, Tia et al., "Wireless Medical Sensor Networks in Emergency Response: Implementation and Pilot Results," Proceedings 2008 IEEE International Conference on Technologies in Homeland Security (2008).
Gaynor, Mark et al., "Integrating Wireless Sensor Networks With the Grid," IEEE Internet Computing pp. 32-39 (Jul./Aug. 2004).
Lin, Shu et al., "Error Control Coding Fundamentals and Applications" pp. 443-504 (1983).
McKenzie, Alexander, "Where Would You Like to Have Your Heart Attack?" IEEE Spectrum pp. 44-50 (Oct. 1971).

(56) References Cited

OTHER PUBLICATIONS

Moore, Dr. Tim, "Wireless Technology Choices Abound for Medical Monitoring," RTC Magazine (Jan. 2005).
Motorola, Inc., "C.O.R. HT-220 'Handie-Talkie' FM Radio," 4 pages. (copyright 1972).
Philips Electronic North America Corporation's Initial Disclosure of Invalidity and Non-Infringement Contentions (Civil Action No. 12-cv-10536 (D. Mass.)) (Aug. 14, 2012).
Philips Electronic North America Corporation's Initial Disclosure of Invalidity and Non-Infringement Contentions Exhibit A (Civil Action No. 12-cv-10536 (D. Mass.)) (Aug. 14, 2012).
Rieckert H. et al., "Telemetry of Venous Blood Pressure at Rest and at Muscle Activity During Running," Biotelemetry International Symposium, Nijmegen, Netherlands pp. 179-182 (May 5-8, 1971).
Stross, Randall, "Tracking Vital Signs, Without the Wires," The New York Times (Sep. 3, 2011).
Swedish Telecom Radio, "Mobitext System Description," pp. 1-12 (1986).
Unversity of Alabama, "WHMS—Wearable Health Monitoring Systems," http://www.ece.uah.edu/~jovanov/whrms/.
Vrincianu, Radu, "Electro-Rheocardiotelemetric Device for Complex Monitoring of the Dynamics and Efficiency of Cardiac Contraction," pp. 196-201.
LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 2 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 3 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 4 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 5 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 6 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 7 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 8 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 9 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 10 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 11 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 12 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 13 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 14 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 15 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 16 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Appendix 17 to LifeWatch Services, Inc.'s LPR 2.3 and 2.4 Initial Non-Infringement, Unenforceability, and Invalidity Contentions (Civil Action No. 11-cv-3619 (N.D. Ill.) May 15, 2012).
Bhargava, Vijay K. et al. "Coding Theory and its Applications in Communications Systems," 43 Defence Science Journal No. 1 pp. 59-69 (Jan. 1993).
Kousa, Maan A. et al., "An Adaptive Error Control System Using Hybrid ARQ Schemes," 39 IEEE Transactions on Communications No. 7 pp. 1049-1057 (Jul. 1991).
Le-Ngoc T. et al., "A CSMA/CD Portable Data System Using Adaptive Reed-Solomon Coding," IEEE 42nd Vehicular Technology Conference pp. 819-22 (1992).
Mackay, R. Stuart "Biomedical Telemetry: The Formative Years," 2 IEEE Engineering in Medicine and Technology No. 1 pp. 11-17 (Mar. 1983).
Tannenbaum, Andrew S., "Structured Computer Organization," Prentice-Hall, Inc., Englewood Cliffs, New Jersey (1976).
"The Third Decade of Cardiac Pacing," (ed. Barold, S. et al.) Futura Publishing Company, Mount Kisco, New York (1982).
"An 8-bit Microcomputer with Analog Subsystems for Implantable Biomedical Application," IEEE Journal of Solid-State Circuits, vol. 24, No. 2 (Apr. 1989) pp. 292-300.
Ayivorth, S. C. and Photiades, D. P., "Telemetering of Various Parameters from Restrained Small animals in the Norma Activity-Rest Cycle," Biotelemetry International Symposium, Nijmegen, Netherlands, pp. 412-417; May 5-8, 1971.
Benetato, Gr., Adamache, A., Vrincianu, R. And Ionescu, Val., "Homeostatic Variations During Work as Determined by Bioradiotelemetry in Metallurgy-Workers,"; Biotelemetry International Symposium, Nijmegen, Netherlands, pp. 226-233; May 5-8, 1971.
Benetato, Gr., Ionescu, Val., Vrincianu, R. and Adamache, A., "Identification of Work Straining Factors in Engine and Car Drivers by Complex" Biotelemetry International Symposium, Nijmegen, Netherlands, pp. 216-225; May 5-8, 1971.
"Biomedical Telemetry," Engineering in Medicine and Biology vol. 2. No. 1 (Mach 1983) pp. 11-17.
Black-Cleworth, Patricia and Verberne, Gerda, "Telemetered EEG and Neuronal Spike Activity in Olfactory Bulb and Amygdala in Free Moving Rabbits," Biotelemetry International Symposium, Nijmegen, Netherlands, pp. 317-325; May 5-8, 1971.
Bogdanski, K. A. and Ruszczynska, M. B., "Measurements of the Ultraweak Bioluminescence Phenomena as a New Biotelemetric Method,"; Biotelemetry International Symposium, Nijmegen, Netherlands, pp. 365-368; May 5-8, 1971.
Bojsen, J., Wallevik, K. and Moller, U., "An Implantable Radiotelemetrical Measuring Device for Simultaneous Long Term Measurements of Body Temperature and Turnover of Rabbit Serum Albumin In Unrestrained Rabbits," Biotelemetry International Symposium, Nijmegen, Netherlands, pp. 337-344; May.
Borbely, Alexander A., Baumann, Isabel and Waser, Nickolas M., "Multichannel Telemetry of Physiological Parameters (Body Temperature, EKG, EEG) in the Rat: II. Applications in Neuropharmacology," Biotelemetry International Symposium, Nijmegen, Netherlands, pp. 381-388; May 5-8, 1971.
Bornhausen, M., Matthes, R. and Kimmich, H.P., "Infrared Light and Biomedical Telemetering in Europe," International Telemetering Conference, vol. 20, pp. 809-816; Oct. 22-25, 1984.
Boter, J. and Kuiper, J., "Ways to Avoid Noise and Artifacts When Using Telemetry," Biotelemetry International Symposium, Nijmegen, Netherlands, pp. 267-275; May 5-8, 1971.
"Cardiocomandor' an Electronic Portable Schedule Apparatus Used by Top Athletes for Conducting Self Internal Training," by Biotelemetry International Symposium, Nijmegen, Netherlands, pp. 173-175; May 5-8, 1971.
Castelfiori, S. and Dubini, S., "Radiotelemetry System for Fetal Monitoring," Biotelemetry International Symposium, Nijmegen, Netherlands, pp. 237-245; May 5-8, 1971.

(56) References Cited

OTHER PUBLICATIONS

Clasing, D. and Machtens, E., "The Effect of Beta-Adrenergic Blocking Agents on the Heart Rate During Psychic Stress," Biotelemetry International Symposium, Nijmegen, Netherlands, pp. 246-250; May 5-8, 1971.
Cordless Telecommunications in Europe—The Evolution of Personal Communications, May 1990.
Currie, J. C. M., Riddle, H. C.,. and Watson, B. W., "The Use of Telemetry to Study the Physiological and Clinical Variations of Intracranial Pressure in Man," Biotelemetry International Symposium, Nijmegen, Netherlands, pp. 326-331; May 5-8, 1971.
Delhez, L., Gillard, C., Deroanne, R., Pirnay, F. and Petit, J. M., "Electromyographic Analysis of Respiratory Movements by Autonomic Memorization During A 25 m Underwater Dive," Biotelemetry.
Deposition Exhibit 174, in Civil Action No. 04-cv-05944 (N.D. Ill.) Letter from Critikon, Inc., to Center for Devices and Radiological Health Food and Drug Administration, Jul. 9, 1993, pp. 1-4., Videotaped Deposition of Patrick Bradley, La Jolla, CA, Feb. 27, 2006.
Deposition Exhibit 175 in Civil Action No. 04-cv-05944 (N.D. Ill.), Abstract, Videotaped Deposition of Patrick Bradley, La Jolla, CA, Feb. 27, 2006.
Deposition Exhibit 176 in Civil Action No. 04-cv-05944 (N.D. Ill.), Abstract, Videotaped Deposition of Patrick Bradley, La Jolla, CA, Feb. 27, 2006.
Deposition Exhibit 177 in Civil Action No. 04-cv-05944 (N.D. Ill.), Abstract of New PCI, Inc. Acquisition Corporation, Dec. 1992, 1 pg.
Deposition Exhibit 178 in Civil Action No. 04-cv-05944 (N.D. Ill.), Letter from Department of Human Services to FOI Services, Inc., Oct. 27, 1995, 5 pgs.
Deposition Exhibit 179 in Civil Action No. 04-cv-05944 (N.D. Ill.), Review Memorandum from Charles Shang Chan Ho, Ph.D., to The Record, Dec. 23, 1994, 20 pgs.
Deposition Exhibit 181 in Civil Action No. 04-cv-05944 (N.D. Ill.), Letter from Pacific Communications, Inc. to Critikon Central Station Monitor, May 14, 1993, 1 pg.
Deroanne, R., Pimay, F., Servais, J. C. and Petit, J. M., "Telemetry and Ergometry Associated to the Measure of Oxygen Consumption During Sports Events," Biotelemetry International Symposium, Nijmegen, Netherlands, pp. 101-110; May 5-8, 1971.
Evans, Brian T., B.Sc., "A Remotely Operated ECG Telemeter for Chronic Implantation in Rats," Biotelemetry International Symposium, Nijmegen, Netherlands, pp. 353-359; May 5-8, 1971.
"External Transcutaneous Pacemakers," Annals of Emergency Medicine (vol. 18 No. 12) (Dec. 1989) pp. 1280/45-51.
Fernald, Kenneth W., Cook, Todd A., Miller III, Thomas K., Paulos, John J., "A Microprocessor-Based Implantable Telemetry System," Computer, Mar. 1991, pp. 23-30.
Fernald, Kenneth W., Stackhouse, Blaine A., Paulos, John J. and Miller, Tom K., "A System Architecture for Intelligent Implantable Biotelemetry Instruments," Proceedings of the Annual International Conference of the IEEE Engineering in Medicine and Biology Society, vol. 11, pp. 1411-1412; Nov. 9-12, 1989.
Fryer, Thomas B., Sandler, Harold and Doane, Dougles H., "A Multichannel Electromagnetic Flowmeter Telemetry System," Biotelemetry International Symposium, Nijmegen, Netherlands, pp. 73-82; May 5-8, 1971.
Furukawa, Tomozo, Tsuchida, Yoshikazu, Matsumoto, Goro and Shigezumi, Michihiko , "Technical Improvements in Radiotelemetering of the Electrocardiogram," Biotelemetry International Symposium, Nijmegen, Netherlands, pp. 202-215; May 5-8, 1971.
Gachmann, K. and Zerzawy, R., "Radiotelemetry of Direct Blood Pressure Measurement in Aorta, Pulmonary Artery and Heart," Biotelemetry International Symposium, Nijmegen, Netherlands, pp. 183, 186-187; May 5-8, 1971.
GMP/Wireless Medicine, Inc.'s Answers to Nonin Medical Inc.'s Third Set of Interrogatories (Nos. 4-20) in Civil Action No. 1:04-cv-05944 (N.D. Ill.) dated Jul. 22, 2005 pp. 1-3, 9 and 14.

GMP/Wireless Medicine Inc.'s Responses to Nonin Medical Inc.'s First Set of Requests for Admission (Nos. 1-37) in Civil Action No. 1:04-cv-05944 (N.D. Ill.) dated Nov. 11, 2005.
GMP/Wireless Medicine Inc.'s Responses to Nonin Medical Inc.'s Second Set of Requests for Admission (Nos. 38-65) in Civil Action No. 1:04-cv-05944 (N.D. Ill.) dated Jan. 30, 2006.
GMP/Wireless Medicine Inc.'s Responses to Nonin Medical Inc.'s Third Set of Requests for Admission (Nos. 66-259) in Civil Action No. 1:04-cv-05944 (N.D. Ill.) dated Jan. 31, 2008.
GMP/Wireless Medicine Inc.'s Answers to Nonin Medical Inc.'s Sixth Set of Interrogatories (Nos. 24-35) in Civil Action No. 1:04-cv-05944 (N.D. Ill.) dated Apr. 16, 2007 pp. 1-3, 9, 11-12.
Holter, Norman J., "Storage Telemetry and Sudden Death,"; Biotelemetry International Symposium, Nijmegen, Netherlands, pp. 151-161; May 5-8, 1971.
IEE Journal of Solid-State Circuits, Jun. 1982; vol. SC-117, No. 3.
Ijsenbrandt, H. J. B., Kimmich, H. P., and Van Den Akker, A. J., "Single to Seven Channel Lightweight Biotelemetery System," Biotelemetry International Symposium, Nijmegen, Netherlands, pp. 57-64; May 5-8, 1971.
Ivison, J. M., Hoare, D. W. and Qazi, S., "A Time-Division Multiplexed Telemetry System Using Delta-Modulation," Biotelemetry International Symposium, Nijmegen, Netherlands, pp. 39-48; May 5-8, 1971.
Kimmich, H. Peter, "Biotelemetry," Encyclopedia of Medical Devices and Instrumentation, vol. 1, pp. 409-425 (1988).
Kimmich, H.P., "Biotelemetry, Based on Optical Transmission," Biotelemerty and Patient Monitoring, vol. 9, No. 3, pp. 129-143, 1982.
Kimmich, H.P., "Clinical Telemetry and Patient Monitoring," Biotelemetry II Second International Symposium, Davos, Netherlands, pp. 190-195; May 20-24, 1974.
Kimmich, H.P., "Modern Patient Care Using Biotelemetry: Its Potential and Technical Realization at Present and in the Future," Medical Progress Through Technology, vol. 9, No. 2/3, pp. 85-93, 1982.
Kimmich, H.P., "Multichannel Biotelemetry," International Journal on Biotelemetry and Patient Monitoring, vol. 2, No. 3-4, pp. 207-255, 1975.
Kimmich, H. P., "Oxygen Consumption Measurements During Exercise By Means of Radiotelemetry," Biotelemetry International Symposium, Nijmegen, Netherlands, pp. 130-136; May 5-8, 1971.
Kimmich, H.P. and Ijsenbrandt, H.J.B., "Personal PDM/PCM Biotelemetry System," Biotelemetry II Second International Symposium, Davos, Netherlands, pp. 2-4; May 20-24, 1974.
Kimmich, Hans Peter; "Telemetry of Respiratory Oxygen Pressure in Man," Buhler-Buchdruck, Zurich, Switzerland (1969).
Kimmich, H.P. and Kreuzer, F., "Telemetry of Respiratory Oxygen Pressure in Man at Rest and During Exercise," International Symposium on Oxygen Pressure recording, Nijmegen, Netherlands, vol. 3, pp. 22-41; Sep. 19-20, 1968.
Kimmich, H.P. and Kreuzer, F., "Trends in Biomedical Telemetry and Patient Monitoring,".
Kimmich, H.P. and Vos, J.A., "Single to Seven Channel Lightweight Biotelemetry System," Biotelemetry International Symposium, Nijmegen, Netherlands, pp. 5764; May 5-8, 1971.
Kimmich, H.P. and Vos, J.A., "Telemetry of Respiratory Air Flow," Biotelemetry International Symposium, Nijmegen, Netherlands, pp. 111-120; May 5-8, 1971.
Klein, Marcel, Milhaud, Claude and Rebelle, Jacques, "Development an Adjustment of a Multi-Channel Miniaturized FM/AM Telemetering System Adapted to the Primates," Biotelemetry International Symposium, Nijmegen, Netherlands, pp. 83-88; May 5-8, 1971.
Kocnar, K. and Vichr, R., "Mobile Telemetric Equipment For The Transmission of ECG and Respiratory Frequency With Automatic Data Recording," Biotelemetry International Symposium, Nijmegen, Netherlands, pp. 95-98; May 5-8, 1971.
Kozinski, Edward, "Estimation of the Intensity of Physical Exercises in Children and Adolescents Based on Telemetric Studies of Circulatory System," Biotelemetry International Symposium, Nijmegen, Netherlands, pp. 251-255; May 5-8, 1971.
Kristan, L., Dvorak, M., Zacek, I., and Pokorn , F., "Experience with the Application of Biotelemetry (ECG, EMG) Under Strenuous

(56) References Cited

OTHER PUBLICATIONS

Working Conditions in Various Operational Environments," Biotelemetry International Symposium, Nijmegen, Netherlands, pp. 289-297; May 5-8, 1971.
Kudo et. al, "Biotelemetry IX" Eds.: H.P. Kimmich and M. R. Neuman, pp. 55-58, 1987.
Laurig, W. and Rohmert, W., "Telemetric Transmission of Ergonomical and Time Study Data to Describe Work Load of Radar Controllers," Biotelemetry International Symposium, Nijmegen, Netherlands, pp. 397-405 May 5-8, 1971.
Memorandum Opinion and Order (re: claim construction), Civil Action No. 04-cv-05944 (N.D. Il..) Dec. 8, 2008.
Miller III, T. K., Bhuva, Bharat L., Barnes, Russell L., Duh, Jyy-Chiang, Lin, Hsing-Bang and Van den Bout, David E., "The HECTOR Microprocessor," IEEE 1986, pp. 406-411.
Motorola, Performance Specification sheet published for Motorola C.O.R HT-220 Handie-Talkie FM Radio, 2 pages, printed 1971.
Motorola, Performance Specification sheet published for Motorola C.O.R HT-220 Handie-Talkie FM Radio, 2 pages, printed 1973.
Motorola Inc.'s Answers to Nonin Medical Inc.'s Third Set of Interrogatories (Nos. 4-20) in Civil Action No. 1:04-cv-05944 (N.D. III.) dated Jul. 22, 2005 pp. 1, 7-8 and 12.
Motorola Inc.'s Responses to Nonin Medical Inc.'s First Set of Requests for Admission (Nos. 1-37) in Civil Action No. 1:04-cv-05944 (N.D. III.) dated Nov. 11, 2005.
Motorola, Inc.'s Responses to Nonin Medical Inc.'s Third Set of Requests for Admission (Nos. 66-259) in Civil Action No. 1:04-cv-05944 (N.D. III.) dated Jan. 31, 2008.
Neukomm, Peter A, "A Radio-Controlled Monitoring System for Multichannel Telemetry," Biotelemetry, vol. 1, pp. 251-263 (1974).
Nielsen, Jacob Fredelund and Wagner, Gorm, "Implantable FM-Telemetry Transmitters for Registration of Biopotentials," Biotelemetry International Symposium, Nijmegen, Netherlands, pp. 360-364; May 5-8, 1971.
Nonin Medical, Inc.'s Third Supplemental Answers to GMP/Wireless Medicine, Inc.s First Set of Interrogatories (Nos. 1-16) in Civil Action No. 1:04-cv-05944 (N.D. III.) dated Jan. 27, 2006.
Nonin Medical, Inc.'s Fourth Supplemental Answers (including Exhibits A-D) to GMP/Wireless Medicine, Inc.'s First Set of Interrogatories (Nos. 1-16) in Civil Action No. 1:04-cv-05944 (N.D. III.) dated Feb. 27, 2009.
Nonin Medical, Inc.'s Fifth Supplemental Answers to GMP/Wireless Medicine, Inc.'s First Set of Interrogatories (Nos. 1-16) in Civil Action No. 1:04-cv-05944 (N.D. III.) dated May 8, 2009.
Nonin Medical, Inc.'s Second Supplemental Answers to GMP/Wireless Medicine, Inc.'s Second Set of Interrogatories (Nos. 25-32) in Civil Action No. 1:04-cv-05944 (N.D. III.) dated May 8, 2009.
Nonin Medical, Inc.'s Answers to GMP/Wireless Medicine, Inc.'s Fourth Set of Interrogatories (Nos. 25-32) in Civil Action No. 1:04-cv-05944 (N.D. III.) dated Oct. 8, 2007.
Nonin Medical, Inc.'s First Supplemental Answers (including Exhibits E-G) to GMP/Wireless Medicine, Inc.'s Fourth Set of Interrogatories (Nos. 25-32) in Civil Action No. 1:04-cv-05944 (N.D. III.) dated Feb. 27, 2009.
Pacific Communications, Inc., "Wireless Connectivity," pp. 5-8 of 56, cited in Civil Action No. 1:04-cv-05944 (N.D. III.); Document 62-2; filed Jan. 24, 2006; (Nonin 018517-018520).
Photiades, D. P., and Ayivorth, S. C., "A Quick and Inexpensive Method of Monitoring on Tape the Heart Rate During Exposure of the Human Head to Pulsed Magnetic Fields,"; Biotelemetry International Symposium, Nijmegen, Netherlands, pp. 168-172; May 5-8, 1971.
Pircher, Louis A., "Telemetry of Cardiovascular Parameters on Fighter Aircraft Flying Pilots," Biotelemetry International Symposium, Nijmegen, Netherlands, pp. 406-411; May 5-8, 1971.
Priebe, L., "Telemetric Measurement of Local Blood Flow by Heat Conduction Probes," Biotelemetry International Symposium, Nijmegen, Netherlands, pp. 65-72; May 5-8, 1971.
Rosenbrock, F. and Rohmert, W., "Multidimensional Coding for Telemetric Transmission of Work Load Factors in Ergonomics Research," Biotelemetry International Symposium, Nijmegen, Netherlands, pp. 389-396 May 5-8, 1971.
Rous, J. and Kocnar, K., "Telemetrical Measurements During Sport Performance on Sportsmen with Cardiac Arrythmias" Biotelemetry International Symposium, Nijmegen, Netherlands, pp. 256-263 May 5-8, 1971.
Salmons, S., "A Telemetric Technique for Measuring Muscle Tension in Conscious, Unrestrained Animals," Biotelemetry International Symposium, Nijmegen, Netherlands, pp. 335-336; May 5-8, 1971.
Sandler, H., Fryer, T. B. and Westbrook, R. M., "Single and Multichannel Implanted Telemetry Systems," Biotelemetry International Symposium, Nijmegen, Netherlands, pp. 345-352; May 5-8, 1971.
Schild, J.H., et al. "A Low Power Multi Channel Biotelemeter," Proceedings of the Seventh Annual Conference of the IEEE Engineering in Medicine and Biology Society—Sep. 1985, Chicago (US) pp. 1205-1210.
Skutt, H. Richard, Fell, Roger B. and Hagstrom, Earl C., "A Multichannel Ultrasonic Underwater Telemetry System," Biotelemetry International Symposium, Nijmegen, Netherlands, pp. 30-38; May 5-8, 1971.
Skutt, H. Richard, Kertzer, Robert and Fell, Roger B., "The Use of Telemetry to Obtain Physiological Data During Exercise," Biotelemetry International Symposium, Nijmegen, Netherlands, pp. 21-29; May 5-8, 1971.
Stalberg, E. and Kaiser, E , "Long-Term EEG-Telemetry," Biotelemetry International Symposium, Nijmegen, Netherlands, pp. 307-316; May 5-8, 1971.
Unold, E.M., Neukomm, P.A. and Nigg, B.M., "Continuous Acceleration Measurements in Humans During Locomotions on Different Surfaces," Biotelemetry II Second International Symposium, Davos, Netherlands, pp. 112-114; May 20-24, 1974.
Vliegenthart, a., "A One Channel Telephone Telemetry System Using Acoustic Couplers," Biotelemetry International Symposium, Nijmegen, Netherlands, pp. 89-94; May 5-8, 1971.
Voegeli, F. and Kraft, W., "Multichannel Telemetry of Physiological Parameters (Body Temperature, ECG, EEG) in the Rat: I. Design and Methods," Biotelemetry International Symposium, Nijmegen, Netherlands, pp. 371-380; May 5-8, 1971.
Vos, J. A., Kimmich, H. P. and Kreuzer, F., "Investigations During Exercise with an Improved $PO_2$ Telemetry System," Biotelemetry International Symposium, Nijmegen, Netherlands, pp. 121-129; May 5-8, 1971.
Vos, J. A. and Kimmich, H. P., "Telemetry of Biomechanical Forces During Exercise," Biotelemetry International Symposium, Nijmegen, Netherlands, pp. 279-288; May 5-8, 1971.
Wagner, Gorm, Hrynczuk, J. R., and Nielsen, J. F., "EMG From Smooth Musculature (Uterus, Ureter, Gut) in Unrestrained Animals Monitored by Telemetry," Biotelemetry International Symposium, Nijmegen, Netherlands, pp. 298-304; May 5-8, 1971.
Wakerly, John , "Error Detecting Codes, Self-Checking Circuits and Applications" 1978: Elsevier North-Holland, Inc., New York City, New York, USA.
Weller, C. and Manson, G., "Three Channel Telemetry System, Compatible With the British Medical and Biological Telemetry Regulations," Biotelemetry International Symposium, Nijmegen, Netherlands, pp. 13-20; May 5-8, 1971.
Wilson-Davies, C. C., "Multi-Channel Telemetry of Cardiovascular Data," Biotelemetry International Symposium, Nijmegen, Netherlands, pp. 234-236; May 5-8, 1971.
Zerzawy, R. and Bachmann, K., "A Programmable Four Channel System for Long-Time Radio Telemetry of Biomedical Parameters," Biotelemetry International Symposium, Nijmegen, Netherlands, pp. 49-56 May 5-8, 1971.
Telecommunications Industry Association, EIA/TIA Interim Standard "Cellular System Dual-Mode Mobile Station—Base Station Compatibility Standard IS-54-B", Apr. 1992 (303 pages).
Telecommunications Industry Association, TIA/EIA Interim Standard "Mobile Station—Land Station Compatibility Standard for Dual-Mode Narrowband Analog Cellular Technology IS-88", Jan. 1993 (113 pages).

(56) References Cited

OTHER PUBLICATIONS

Telecommunications Industry Association, TIA/EIA Interim Standard "Mobile Station-Base Station Compatibility Standard for Dual-Mode Wideband Spread Spectrum Cellular System TIA/EIA/IS-95", (664 pages) (Jul. 1993).
Sansen, Willy M.C. "On the Integration of an Internal Human Conditioning System", IEEE Journal of Solid-State Circuits Council, vol. SC-17, No. 3 pp. 513-521 (Jun. 1982).
Tuttlebee, Wally, "Cordless Telecommunications in Europe, The Evolution of Personal Communications," (161 pages) (copyrighted 1990).
Brinkman, William F. et al., "A History of the Invention of the Transistor and Where It Will Lead Us", 32 IEEE Journal of Solid-State Circuits, vol. 32, No. 12, pp. 1856-1865 (Dec. 1997).
Fuller, J.L., et al., "The Radio Inductograph—A Device for Recording Physiological Activity in Unrestrained Animals", vol. 108 Science pp. 287-288 (Sep. 1948).
Thon, Lars E. "50 Years of Signal Processing at ISSCC," 2003 IEEE International Solid-State Circuits Conference, pp. S20-S21 (2009).
Gordon, Pat L., et al, "Multiprogrammable Pacemaker Technology—A Tutorial Review and Prediction" The Third Decade of Cardiac Pacing, pp. 127-143 (Copyrighted 1982).
Severinghaus, John W., "Takuo, Aoyagi: Discovery of Pulse Oximetry," vol. 105 Anesthesia and Analgesia No. 6 (pp. S1-S4) (Dec. 2007).
Association for the Advancement of Medical Instrumentation, "American National Standard for Cardiac Monitors, Heart Rate Meters and Alarms" from "AAMI Standards and Recommended Practices", 1987 Reference Book, pp. 65-106 (1986).
Severinghaus, John W. et al, "Recent Developments in Pulse Oximetry," 76 Anesthesiology No. 6 (pp. 1018-1038) (Jun. 1992).
Annovazzi-Lodi, Valerio et al., "An Optoelectronic Interconnection for Bidirectional Transmission of Biological Signals", 35 IEEE Transactions on Biomedical Engineering No. 8 (pp. 595-606) (Aug. 1988).
Dorman, Michael Gerard, "An IC-Based Telemetry System for Neurophysiology," (dissertation Standard University) (266 pages) (Apr. 1985).
Berson, Alan S. et al., "Precision Requirements for Electrocardiographic Measurements Computed Automatically," BME-24 IEEE Transactions on Biomedical Engineering No. 4 (pp. 382-385) (Jul. 1977).
Fernald, Kenneth W. et al., "WP4.4: An Implantable Digital Telemetry Integrated Circuit Using an Automatic Resonant-Frequency Search Technique," 1992 IEEE International Solid-State Circuits Conference (pp. 68-69).
Schroeppel, Edward A., "Current Trends in Cardiac Pacing Technology," 1 Biomedical Science and Technology No. 3 (pp. 89-102) (Jul. 1992).
Budinger, Thomas F., "Biomonitoring with Wireless Communications," 5 Annual Review Biomedical Engineering (pp. 383-412) (2003).
Nyquist, H., "Certain Topics in Telegraph Transmission Theory" Presented at the Writer Convention at the A.I.E.E., (pp. 617-644) (Feb. 1928).
Bhatt, Sid et al., "Holter Monitoring Using Implanted Pacemakers," The Third Decade of Cardiac Pacing (ed. S. Serge Barold, et al.) pp. 333-343 (1982).
Mouly, Michel et al., "The GSM System for Mobile Communications" (701 pages) (1992).
Carr, Joseph J. et al., "Introduction to Biomedical Equipment Technology," (610 pages) ($2^{nd}$ ed. 1993).
Geddes, L.A. et al., "Principals of Applied Biomedical Instrumentation", p. 1-13, 95-155, 276-411 ($2^{nd}$ ed. 1975).
Neuman, Dr. Michael, et al., "Physical Sensors for Biomedical Applications," pp. 67-81 (1980).
Lin, Shu et al, "Error Control Coding Fundamentals and Applications," pp. 1-15 and 458-497 and 532-599 (1983).
Smith, David R., "Digital Transmission Systems," ($3^{rd}$ ed. 2004).
Carr, Joseph J. et al., "Introduction to Biomedical Equipment Technology," pp. 238-256 (1981).
Association for the Advancement of Medical Instrumentation "American National Standard for Cardiac Monitor, Heart Rate Meters and Alarms" from "Essential Standards for Biomedical Equipment Safety and Performance" pp. 61-102 ($2^{nd}$ ed. 1988).
Pistoia, Gianfranco, "Batteries for Portable Devices," pp. 33-76 (2005).
Garratt, G.R.M, "The Early History of Radio from Faraday to Marconi" (1994).
Evans, David S. et al., "Invisible Engines—How Software Platforms Drive Innovation and Transform Industries," pp. 183-212 (2006).
Vaucher, Cicero S., "Architecture for RF Frequency Synthesizers" (forward) (2002).
Cohn Dr. Peter, et al, "Fighting the Silent Killer—How Men and Women Can Prevent and Cope with Heart Disease Today" pp. 18-43 (1993).
Anderson, John B. et al., "Source and Channel Coding—an Algorithmic Approach" pp. 107-112 (1991).
Shannon, Claude E., "Communications in the Presence of Noise," 86 Proceedings of the IEEE No. 2 pp. 447-457 (Feb. 1998).
Shannon, Claude E., "A Mathematical Theory of Computation," (1948).
Lee, T.H. "Performance Analysis of Efficient Concatenated Coding Scheme for ARQ Protocols," 138 IEEE Proceedings-1 No. 3, pp. 148-152 (Jun. 1991).
Reed, I.S. et al., "Polynomil Codes Over Certain Finite Fields" 8 J Soc. Indust. Appln. Math. No. 2 pp. 300-304 (Jun. 1990).
Marvasti, Farokh et al., "The Fundamental Theorem of Information Theory From the Sampling Theorem Point of View" IEEE 1992 ICC '92 pp. 344-347.
Burgess, Larry, "Matching RFIC Wireless Transmitters to Small Loop Antennas," High Frequency Electronics, pp. 20-28 (2005).
Wong, Peter, "The Performance of the CT2 System for Data Services," IEEE 1994, pp. 701-704 (Copyright 1994).
Steinbock, Dan, "The Mobile Revolution—The Marking of Mobile Services Worldwide," pp. 34-63 (2005).
Lambert, Laura, "The Internet: A Historical Encyclopedia: Biographies" pp. 143-148 (Copyright 2005).
Poole, Hilary W. et al., "The Internet: A Historical Encyclopedia: Chronology" pp. 43-63 (Copyright 2005).
Chen, Hsiao-Hwa "The Next Generation CDMA Technologies," pp. 177-228 (Copyright 2007).
Petersen, Julie K. "The Telecommunications Illustrated Dictionary $2^{nd}$ edition" pp. 823-825 (Copyright 2002).
McKean, Brian D. et al., "A Telemetry Instrumentation System for Chronically Implanted Glucose and Oxygen Sensors," 35 IEEE Transactions on Biomedical Engineering No. 7, pp. 526-532 (Jul. 1998).
Fernald, Kenneth W. et al., "A Self Tuning Digital Telemetry IC for Use in a Microprocessor-Based Implantable Instrument," 27 IEEE Journal of Solid-State Circuits No. 12, pp. 1826-1832 (Dec. 1992).
"Transmission Networks" pp. 33-34, (1997).
Hamming, R.W. "Error Detecting and Error Correcting Codes," 29 Bell System Technical Journal No. 2 (Apr. 1950).
U.S. International Trade Commission, "Global Competitiveness of U.S. Advanced-Technology Industries: Cellular Communications", pp. 4-1 to 4-21 (1993).
Federal Trade Commission, "To Promote Innovation: The Proper Balance of Competition and Patent Law and Policy" (2003).
Federal Communications Commission Office of Engineering and Technology, "Questions and Answers About Biological Effects and Potential Hazards of Radiofrequency Electromagnetic Fields," OET Bulleting 56 ($4^{th}$ ed.) (1999).
Telecommunication Standardization Sector of International Telecommunication Union, "Data Communication over the Telephone Network: Error Correcting Procedures for DCEs Using Asynchronous-to-Synchronous Conversion," Recommendation V. 42 (1993).
Information Sciences Institute, "Transmission Control Protocol, DARPA Internet Program Protocol Specification," (1981).
Kudo, N. et al., "Optical Biotelemetry Using Indirect Light Transmission," Biotelemetry IX (eds. H.P. Kimmich and M.R. Neuman), pp. 55-58 (1987).

(56) References Cited

OTHER PUBLICATIONS

Schild, J.H. et al., "A Low-Power Multichannel Biote" IEEE/Seventh Annual Conference of the Engineering in Medicine and Biology Society, pp. 1205-1210 (1985).
Request for Reexamination of U.S. Patent No. 6,289,238, 414 pages, (Jul. 22, 2012).
Request for *Ex Parte* Reexamination Under 37 C.F.R. §1.510 of U.S. Patent No. 6,289,238, 657 pages, (Aug. 13, 2013).
Request for Reexamination of U.S. Patent No. 7,215,991, 412 pp. ( Jun. 22, 2012).
Request for *Ex Parte* Reexamination Under 37 C.F.R. §1.510 of U.S. Patent No. 7,215,991, 710 pages, (Aug. 13, 2013).
Bradley, Patrick, Videotaped Deposition, La Jolla, CA, Feb. 2006.
Deposition Exhibit 173 in Civil Action No. 04-cv-05944 (N.D. Ill.) "Wireless Connectivity," by Pacific Communication, Inc., Real-Time Spread Spectrum, 4 pgs., 1993, Videotaped Deposition of Patrick Bradley, La Jolla, CA, Feb. 27, 2006.
Deposition Exhibit 174, in Civil Action No. 04-cv-05944 (N.D. Ill.) Letter from Critikon, Inc., to Center for Devices and Radiological Health Food and Drug Administration, Jul. 9, 1993, pp. 1-4, Videotaped Deposition of Patrick Bradley, La Jolla, CA, Feb. 27, 2006.
Deposition Exhibit 175 in Civil Action No. 04-cv-05944 (N.D. Ill.), Diagram labeled by the witness, Videotaped Deposition of Patrick Bradley, La Jolla, CA, Feb. 27, 2006 1 page.
Deposition Exhibit 176 in Civil Action No. 04-cv-05944 (N.D. Ill.), Color Copy of Observer monitor and Critikon Patient Worn Telemetry, Videotaped Deposition of Patrick Bradley, La Jolla, CA, Feb. 27, 2006 1 page.
Deposition Exhibit 178 in Civil Action No. 04-cv-05944 (N.D. Ill.), Letter from Department of Human Services to POI Services, Inc., Oct. 27, 1995, 5 pgs.
Deposition Exhibit 179 in Civil Action No. 04-cv-05944 (N.D. Ill.), Review Memorandum from Charles Shang Chan Ho, Ph.D., to The Record, VitalCom, Dec. 23, 1994, 20 pgs.
Deposition Exhibit 180 in Civil Action No. 04-cv-05944 (N.D. Ill.), Memorandum from Biomedical Engineer, PEDB, to Record, ODE/DCRND, date Sep. 10, 1993, 6 pgs.
Deposition Exhibit 182 in Civil Action No. 04-cv-05944 (N.D. Ill.), Abstract, Deposition of Michael David Stoop, Mar. 1, 2006.
Judson, Donald William, Deposition of, Irvine, CA, Feb. 2006.
Memorandum Opinion and Order (re: claim construction), Civil Action No. 04-cv-05944 (N.D. Ill.) Dec. 8, 2008.
McBride, William Christian, Deposition of, Irvine, CA, Feb. 2006.
*Motorola, Inc. and GMP/Wireless Medicine, Inc.'s* vs. *Nonin Medical, Inc.*, Expert Report Relating to Invalidity by Charles D Knutson with Exhibits, 04-cv-05944 (N.D. Ill.), dated Oct. 20, 2009, 190 pages.
Stoop, Michael David, Deposition of, Irvine, CA, Mar. 2006.
Philips Electronic North America Corporation's Initial Disclosure of Invalidity and Non-Infringement Contentions Exhibit B (Civil Action No. 12-cv-10536 (D. Mass.)) (Aug. 14, 2012).
Philips Electronic North America Corporation's Initial Disclosure of Invalidity and Non-Infringement Contentions Exhibit C (Civil Action No. 12-cv-10536 (D. Mass.)) (Aug. 14, 2012).
Declaration in Support of Petition to Make Special Under 37 CRF § 1.102(d) Based on Infringement as Defined in MPEP 708.02(II), Patent 7,215,991 File History, Mar. 25, 2004.
Petition to Make Special Under 37 CFR § 1.102(d) Based on Infringement as Defined in MPEP 708.02 (II), Patent 7,215,991 File History, Mar. 25, 2004.
"The Third Decade of Cardiac Pacing: Advances in Technology and Clinical Applications," (ed. Barold, S. et al.) Futura Publishing Company, Mount Kisco, New York, ISBN 0-87993-159-0 (1982).
Akselsen, Sigmund et al., "Telemedicine and ISDN," IEEE Communications Magazine (Jan. 1993) pp. 46-51.
Bhargava, Vijay K. et al. "Coding Theory and its Applications in Communications Systems," vol. 43, Defense Science Journal No. 1 pp. 59-69 (Jan. 1993).
Bryan, John "Data Over Cellular-Enhanced Throughput Cellular Makes you Forget That Your Data is Riding on an Analog Connection," 19 BYTE No. 9 (Sep. 1, 1994).
ITU-T/CCITT, Telecommunication Standardized Sector of ITU, "Data Communication Over the Telephone Network-A Family of 2-Wire, Duplex Modems Operating at Data Signalling Rates of up to 9600 bit/s For Use On The General Switched Telephone Network and on Leased Telephone-Type Circuits-Recommendation V.32," 27 pages. (Mar. 1993).
CCITT—The International Telegraph and Telephone Consultative Committee, "Data Communication Over the Telephone Network-A Duplex Modem Operating at Data Signalling Rates of Up to 14 400 bit/s for Use on the General Switched Telephone Network and on Leased Point-to-Point 2-Wire Telephone-Type Circuits-Recommendation V.32 bis," pp. 1-22 (1991).
Cook, T., Fernald, Kenneth, W., Miller, Thomas K. and Paulos, John J., "A Custom Microprocessor for Implantable Telemetry Systems," Third Annual IEEE Symposium on Computer-Based Medical Systems, pp. 412-417; Jun. 3-6, 1990.
Fernald, Kenneth W., Thesis: "A Microprocessor-Based system for the Fast Prototyping of Implantable Instruments for Biomedical Research Applications," North Carolina State University, 1992.
Hamming, Richard W., "Coding and Information Theory," 1980: Prentice-Hall, Englewood Cliffs, New Jersey, USA.
Hodges, M, "The GSM Radio Interface," Br Telecom Technol J vol. 8, No. 1, Jan. 1990, p. 31-43.
Marvasti, Farokh et al., "The Fundamental Theorem of Information Theory From the Sampling Theorem Point of View" IEEE 19921CC '92 pp. 344-347.
McKee, James J. et al. "A Simultaneous Full-Duplex Speech and Electrocardiogram Communications System," Engineering in Medicine and Biology Society, 1994. Engineering Advances: New Opportunities for Biomedical Engineers. Proceedings of the 16th Annual International Conference of the IEEE pp. 902-903 (1994).
Mouly, Michel et al., "The GSM System for Mobile Communications," ISBN 2-9507190-0-7, (701 pages) (1992).
Nyquist, H., "Certain Topics in Telegraph Transmission Theory," Proc. IEEE, vol. 90, No. 2, Feb. 2002.
Operator's Manual, Chapter 1, PCI Wireless System, (Apr. 29, 1994).
Pacific Communications, Inc., "Wireless Connectivity," pp. 5-8 of 56, cited in Civil Action No. 1:04-cv-05944 (N.D. Ill.); Document 62-2; filed Jan. 24, 2006.
Powers, Clifton C., Thesis: "A Base Station Receiver for Biomedical Telemetry," North Carolina State University, 1991.
Snyder, Alan J. et al. "A Secure Communications and Status Reporting Protocol for Implanted Devices," Sixth Annual IEEE Symposium on Computer-Based Medical Systems (copyright 1993) pp. 253-257.
Stackhouse, Blaine A., Thesis: "A Transmitter Circuit Design for an Implantable Biomedical Chip Set," North Carolina State University, 1989.
Televerket, "Mobitex System Description," The Swedish Telecommunications Administration, (1985).
Thorborg, Sten et al. "Mobimed—A Telemedicine System for Mobil Monitoring of Physiological Parameters," SPIE Vo. 1355 Telecommunication for Health Care: Telemetry, Teleradiology, and Telemedicine (1990) pp. 3235.
Wakerly, John, "Error Detecting Codes, Self-Checking Circuits and Applications" 1978: Elsevier North-Holland, Inc., New York City, New York, USA.
Webster, J., "Encyclopedia of Medical Devices and Instrumentation," John Wiley & Sons, 1988. 19 pages.
GMP/Wireless Medicine, Inc.'s Opening Brief Re: Construction of Certain Patent Claim Terms, Civil Action No. 1:04-cv-05944, N.D. Ill., Filed Apr. 14, 2008, 27 pages.
GMP/Wireless Medicine, Inc.'s Memorandum in Response to Nonin's Opening Memorandum in Support of Claim Construction, Civil Action No. 1:04-cv-05944, N.D. Ill., Filed May 5, 2008, 52 pages.
Taped Deposition of: Marcus Besson, Non-Confidential Portion, Civil Action No. 1:04-cv-05944, N. D. Ill., Filed May 5, 2008, 7 pages.
Plaintiff Body Science LLC's Initial Infringement Contentions, Civil Action No. 1:12-cv-10536, D. Mass., filed Jun. 15, 2012, 40 pages.

(56) References Cited

OTHER PUBLICATIONS

In Re Body Science LLC Patent Litigation, Reply to Defendants' Responses in Opposition to Plaintiff's Motion to Transfer Actions to the Northern District of Illinois Pursuant to 28 U.S.C. § 1407 for Coordinated Pretrial Proceedings, Filed May 17, 2012, 19 pages.

Exhibit K, Deposition of Dr. Ralph Bax, Apr. 21, 2006, 5 pages.

Exhibit L, Deposition of Gotthart von Czettriz, Apr. 21, 2006, 2 pages.

\* cited by examiner

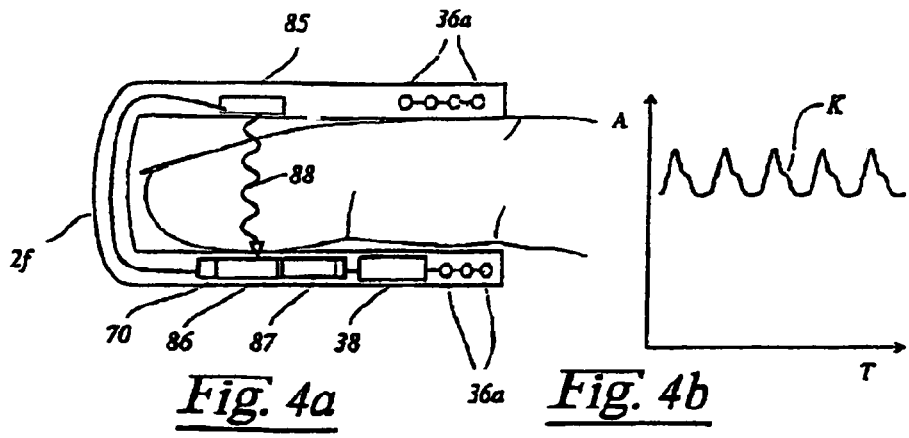
*Fig. 4a*    *Fig. 4b*
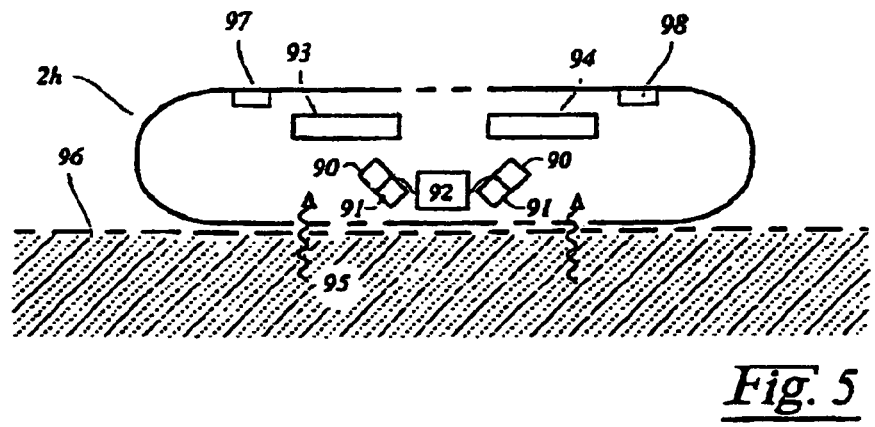
*Fig. 5*
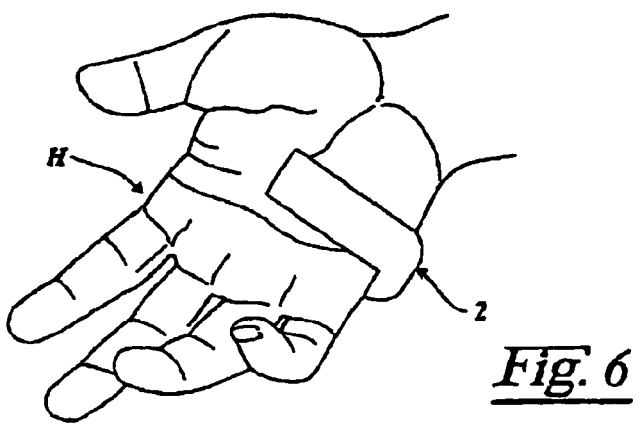
*Fig. 6*

WIRELESS MEDICAL DIAGNOSIS AND MONITORING EQUIPMENT

This application is a continuation of U.S. patent application Ser. No. 10/396,621 filed on Mar. 24, 2003, now U.S. Pat. No. 7,215,991, which is a continuation of U.S. patent application Ser. No. 09/882,152 filed Jun. 15, 2001, now U.S. Pat. No. 6,577,893, which is a continuation of U.S. patent application Ser. No. 09/379,763 filed Aug. 24, 1999, now U.S. Pat. No. 6,289,238, which is a continuation of U.S. patent application Ser. No. 08/985,673, filed Dec. 5, 1997, now U.S. Pat. No. 5,957,854, which is a continuation of U.S. patent application Ser. No. 08/605,197, filed Mar. 1, 1996, now U.S. Pat. No. 5,862,803, which is a national stage application filed under 35 U.S.C. 371 International Application No. PCT/EP94/02926 filed Sep. 2, 1994, which claims priority to German Patent Application No. P 43 29 898.2 filed Sep. 4, 1993.

BACKGROUND

The invention relates to a medical measured-data acquisition equipment for monitoring and diagnosis, in particular to EEG and EKG equipment, as well as to facilities for controlling the breathing, the O2 saturation content in the blood, the body temperature, and for recording electric potentials or electrodermal activities such as the SSR (sympathetic skin response). Such monitoring and diagnostic equipment is used mainly in intersjve- care stations in hospitals, or in the examination of patients.

Monitoring equipment is used also for monitoring infants at home, among other things. In the Federal Republic of Germany about 2000 infants die annually from the sudden infant death syndrome, a phenomenon, the causes of which have not yet been elucidated in spite of intensive research. However, everything speaks for the fact that the sudden infant death is to be attributed to a failure of the respiratory function (apnea), and possibly of the cardiac function. It exclusively occurs during sleeping. The only preventive measure for preventing the sudden infant death currently consists in the monitoring of the respiratory or cardiac function. Said procedure is useful in that by stimulating the infant immediately following failure of the respiratory function, the respiratory activity automatically starts again, with a few exceptions.

EKG and EEG facilities assume a special position among monitoring and diagnostic devices because their high medical conclusiveness. An electrocardiogram (EKG) is the recording of the time curve of heart action potentials; an electroencephalogram (EEG) is the graphic record of the brain action potentials. The analysis of the EKG's and EEG's supplies important information about the heart or brain function of the patient.

Conventional monitoring and diagnostic equipment is structured in such a way that one or several electrode(s) is/are mounted on the patient, which tap the respective signals (predominantly potential and impedance values) and transmit such signals via cables to amplifier units. Normally, separate electrodes are used for each measurement parameter.

Especially in EKG and EEG examinations, many cables are suspended on the patient, connecting the EKG/EEG-electrodes with the evaluator units, which process and record the signals. Such cables obstruct the patient and highly limit his or her freedom of movement, and, therefore, are only conditionally suitable especially for carrying out examinations at stress (e.g. EKG's at stress). In addition, due to the stiffness of the cables and the lever forces connected therewith, the cables become easily detached particularly when the patient moves.

Furthermore, in connection with infants, there is the risk that they may play with the cables and detach the glued-on electrodes.

The electrode cables are especially troublesome in connection with home or hospital monitoring of infants. The removal and reattachment of the electrodes is troublesome especially when garments are changed frequently (e.g. during the changing of diapers).

Furthermore, in complicated examinations with a great number of measured quantities such as, for example, in the polysomnography in connection with infants, problems arise on account of the fact that many relatively large electrodes have to be attached to the patient. Moreover, it is necessary in this connection to take into account the psychic stress of the patient, who is connected to an electrical device via a great number of cables. Such psychic stress may have a bearing on both the physical stressability and the physiological characteristic lines.

The above-described methods are high in expenditure, user-unfriendly, and under certain circumstances may require certain medical expertise, for example as far as the arrangement of all sorts of different electrodes is concerned. They are consequently only conditionally suitable especially for use at home, for example for the long-term monitoring of infants. In addition, there is the increased risk of falsified data and alarm malfunction because due to the simple electrode structure, it is not possible to make a distinction between medical abnormalities and technical defects (e.g. detached electrodes).

Therefore, there is need for a nonelectric connection between the electrodes connected to the patient and the equipment. Furthermore, due to the galvanic separation of the electrodes from the evaluation station, the safety of the patient is assured as well.

Telemetry systems for biosignals, in connection with which the EKG- or EEG-data tapped on the patient are transmitted via electromagnetic waves (preferably in the infrared range), are described, for example in "Biotelemetrie IX" (publishers: H. P. Kimmich and M. R. Neumann, 1987, pp. 55-58). The data are transmitted in this connection in the one-way mode from the electrodes to the output unit, i.e., without (error) feedback from the receiver to the emitter. A particular drawback in this connection is that the measured values are transmitted as an analog signal, which means they are relatively susceptible to interference, for example with respect to the 50 Hz-ripple and its harmonics.

A further development for telemetric EKG-measurements is described in laid-open patent specification WO 90/08501, where for achieving a higher transmission rate and data safety, the recorded signals are digitalized, coded (preferably according to the Manchester code, or as FSK (frequency shift keying), and then transmitted electromagnetically or by light wave conductor.

In connection with said telemetric method, the signals of the individual electrodes attached to the body are transmitted via cable to an additional emitter unit, which is separately attached to the body, and transmitted from there by radio or light wave conductor to the evaluator station. However, the above-mentioned methods have the drawback that the emitter unit is supplied with current via batteries. The batteries have to assure not only the power supply for the data recording and data processing, but also for the data transmission via radio transmission. Therefore, the batteries have to be replaced frequently, which is connected with drawbacks especially in long-term monitoring. Since the emitter units are relatively large, said methods again limit the freedom of movement of the patient. No details are specified in the above-mentioned references with respect to the structure of the electrodes used for the signal acquisition.

Measuring probes with HF-energy supply are known, for example from the references DE-OS 32 19 558, U.S. Pat. No. 4,075,632, and WO 92/07505. However, the fields of application of said measuring probes are almost exclusively aimed at the identification of objects, and are implanted for said purpose on the animal or human body. Furthermore, the structure of said device is not suitable for the medical signal acquisition as well as for transmitting such signals, in particular not in connection with a great number of data from one or a plurality of electrode(s), and from a number of patients, if need be. With said methods, the signal transmission takes place almost exclusively via passive telemetry, whereby the measured data are detected in that the measuring probe carries out a modulation absorption in the HF-field of the evaluator station (ES), such absorption acts back on the ES (indirect transmission of information by inductive coupling). Said procedure, however, is suitable only in connection with extremely small spacings between the emitter and the receiver of only a few centimeters (as it is the case especially in connection with implanted probes), and only in the absence of external interferences. Moreover, in connection with said measuring probes, no provision is made for two-way data transmission, i.e., information is transmitted only from the receiver to the transmitter, so that errors in the data transmission can not be compensated, or compensated only highly conditionally.

The invention is based on the problem of making available a reliable monitoring and diagnosis equipment with wireless electrodes, which is suitable for both the use at home and for operation in hospitals. In particular, a safe data transmission of the electrodes is to be assured also when a great number of electrodes are operated simultaneously.

Said problem is solved by the characterizing features of patent claim 1. Preferred embodiments and further developments are specified in the dependent claims.

The proposed bidirectional, digital data transmission results in the surprising effect that the data transmission safety is significantly increased. By transmitting redundant information in the data emitted by the electrodes, the evaluator station is capable of recognizing errors and request a renewed transmission of the data. In the presence of excessive transmission problems such as, for example transmission over excessively great distances, or due to obstacles absorbing the high-frequency radiation, the evaluator station is capable also of controlling the data transmission, or to manipulate on its own the data emitted by the electrodes. As control of the data transmission it is possible to consider, for example an adaptation of the transmitting power of the electrode, or a change of the transmission channel. If the signal transmitted by the electrode is too weak, the evaluator station will transmit to the electrode a command, which increases its transmitting power. However, if the signal transmitted by the electrode is superimposed by other sources of interference, the evaluator station, by changing the channel, is capable of attempting securing a flawless and interference-free transmission. Alternatively, the evaluator station can also cause the electrode to change the data format for the transmission, for example in order to increase the redundant information in the data flow. Due to the increased redundancy, transmission errors can be detected and corrected more easily. In this way, safe data transmissions are possible even with the poorest transmission qualities. Said measure opens in a surprisingly simple way the possibility of reducing the transmission power of the electrode to a considerable extent. This reduces the energy requirement of the electrodes, so that the latter can be used uninterruptedly over longer periods of time. Due to the reduced transmitting power it is possible also to exclude possible biological stresses caused by the electromagnetic waves. Another advantage of the bidirectional digital data transmission lies in the possibility of transmitting test codes in order to filter out external interferences such as, for example, refraction or scatter from the transmission current. In this way, it is possible also to reconstruct falsely transmitted data. Due to the safe data transmission between the electrodes and the evaluator station, the device according to the invention is particularly suitable for use at home such as, for example, far monitoring infants even though no technically trained personnel is available there, as a rule. When used in hospitals, for example for monitoring in intensive care, the device according to the invention offers the special advantage that very many electrodes can be operated at the same time without interferences in one and the same room. Mutual influencing of the electrodes is excluded a priori. In particular, it is possible to program standard electrodes with a great number of sensors via the evaluator station in such a way that such electrodes can be used for special applications, i.e., for special application cases.

The electrodes can be supplied with current by an evaluator station (ES) by means of high-frequency energy transmission (especially in the radio frequency (RF) range). The antennas or optic detectors (e.g. semiconductor diodes) of the electrodes absorb in this connection the high-frequency field (HF-Field) radiated by the evaluator station, the latter being arranged spaced from said electrodes. By means of the power supply unit arranged in the electrode, which unit converts (rectifies) the HF-radiation and stores it, if need be, then supply voltage is then generated for the electrodes.

The device according to the invention can be designed also in such a way that the power supply unit of the electrodes is realized by additional integrated, miniaturized accumulators. A replacement of weak or empty accumulators is not required in connection with the device of the invention because the accumulators are recharged by the high-frequency field radiated by the evaluator station. Charging of the accumulators can be carried out also only temporarily, for example at points in time at which the electrodes are not in use, i.e., outside of the recording of measured values. In this case, the energy for the charging can be transmitted via resonance coupling, for example by means of inductive coupling. Since the accumulators do not have to be replaced, they also can be encapsulated in the electrodes.

Furthermore, it is possible particularly in connection with long-term monitoring to first supply the electrodes with current through the accumulator, and then later—if necessary—supply the electrodes, for example if the accumulators are weak, with current via the emitted HF-frequency field of the evaluator station. In this way, a possible biological stressing of the body by the high-frequency radiation acting on it can be excluded or minimized.

Frequency generation units generate in the electrodes or in the evaluator station the required oscillator frequencies for the emitter units as well as receiving units. Preferably, the frequency generation unit comprises one or a plurality of PLL (phase-locked loop) or FLL (frequency-locked-loop) synthesizers, which generate the various frequencies. The transmission frequencies for the (data) transmission may basically extend from the 100 kHz range (long wave) to the $10^{15}$ Hz-range (optical frequencies). For small electrode dimensions, high bit transmission rates and short transmission distances, transmission frequencies in the UHF range, microwave range and above (>10) MHz, however, are particularly suitable.

It is advantageous for the device according to the invention if micro-structured sensors such as semiconductor sensors or thin-layer sensors are used for the signal detection or signal recording. Semiconductor sensors are characterized by their small size, their sensitivity, their high integration capability, and their low current consumption. Important are particularly sensors which are based on the (field effect) transistor (e.g. Si-MOS-FET), the diode or the capacitor principle. In this way, it is possible to realize a great number of sensors such as, for example, bio- or ion-sensitive sensors (ISFET), acceleration, pressure, voltage, impedance, current, temperature, as well as radiation sensors.

By using semiconductor components as sensors with integrated signal processing, transmitting/receiving (tranceiver) and, if need be, evaluator units, individual circuit arrangements with a number of sensors can be integrated in a chip with edge lengths of less than 10 mm and heights of under 0.5 mm. In this way, the number of electrodes can be reduced, on the one hand, and additional electric components—which are attached to the body and which limit the freedom of movement—can be omitted. Since the distance of transmission from the electrodes to the evaluator station normally amounts to only a few meters (order of magnitude: 1 to 10 m), the energy supply or transmitting power of the electrodes comes, in the ideal case, to only fractions of mW, which means it is completely harmless, medically speaking. The use of miniature batteries (e.g. button cells) is consequently suitable for the energy supply as well, especially for short transmission distances. For this purpose, the TDMA-process is particularly advantageous because the electrodes transmit only at certain time intervals, which means that energy can be saved.

Another feature of the device according to the invention lies in the arrangement of the antenna. The latter is preferably completely (or at least partly) arranged in the electrode covering or electrode diaphragm consisting of, for example flexible plastic. If the electrode is designed in the form of a bracelet, the bracelet can be used as the antenna as well. The antenna can be realized in all sort of ways, for example as a dipole, lagarithmic-periodic, dielectric, strip conduction or reflector antenna. Preferably, the antenna consists of one or a plurality of conductive wires or strips, which are arranged in a spiral form (spiral antenna or also helical antenna). In this way, the antenna can be designed with a relatively large surface area, which requires lower transmission outouts for the data transmission and HF-Supply. In particular, it is possible in the radio transmission to use frequency-selective antennas for separating the transmission and receiving band, and polarization-sensitive antennas in connection with directional transmission. Polarization-sensitive antennas consist of, for example thin metal strips arranged in parallel on an insulating carrier material. Such a structure is insensitive to or permeable to electromagnetic waves with vertical polarization, we es with parallel polarization are reflected of absorbed depending on the design, it is possible to obtain in this way, for example good cross polarization decoupling in connection with linear polarization.

It is possible, furthermore, to integrate the antenna, for example in the frame of the chip, whereby the antenna is preferably realized by means of the thin-layer technology.

The antenna of the electrodes serves both for transmitting the electrode data and for receiving the control data transmitted by the evaluator station, as well as for receiving, if need be, the high-frequency energy (for the energy supply), i.e., basically only one transmitting and receiving antenna is required.

In particular, directional couplers can be arranged on the transmitter outputs of the electrodes and/or the evaluator station, which couplers measure the radiated or reflected (radio transmission) output. Any damage to the antenna (or also any faulty adaptation) thus can be registered, because it is expressed by increased reflection values.

It is possible to carry out the high-frequency energy supply and the data transmission on different frequencies (e.g. data transmission in the IR-range by means of transmitting and receiving semiconductor diodes in the electrodes and evaluator station; energy transmission in the microwave range via the antennas). In particular, it is possible also to transmit sensor data to be transmitted and also electrode control as well as control data from the evaluator station to the electrodes, in each case on different carrier frequencies or at different points in time.

Preferably, the frequency modulation and/or phase modulation is used for the data transmission in order to exclude excessively long zero series, as they may be present in connection with amplitude modulation. With pure HF-supply of the electrodes, (i.e., without the use of accumulators), transmission of the electrode control and transmission control data to the electrodes can take place, for example by modulating the HF-field.

Furthermore, it has to be taken into account that the radio signal power of the transmitted data is subjected in the receiver to certain variations, as may be the supply voltage of the electrodes (for example if the electrodes are exclusively supplied with energy by the high-frequency field (HF) of the evaluator station). This is mainly the case when the patient moves or turns, thereby changing the spacing between the electrodes and the evaluator station. Also, a certain attenuation and scattering of the signals has to be taken into account, among other things, especially in long-term monitoring (for example in the monitoring of infants or patients in intensive care units), because these measurements are then frequently carried out on dressed patients and in the bed (under a blanket). Therefore, a further development of the invention consists in arranging in the evaluator station a control unit for the transmission output. With said control unit, the evaluator unit determines and controls the transmission output received from the individual electrodes, and, if need be, controls its own transmission output accordingly. If, in the evaluator station, the electrode field intensity falls short of a preset lower threshold value, the evaluator station controls the relevant electrode for increasing the transmission output. Preferably, the procedure followed is such that maximum values presentable for the electrode transmission output are not exceeded. For this purpose, the electrode transmits its transmission output to the evaluator station.

For controlling the transmission output of the evaluator station, the electrode contains a reference element for measuring the transmission output received. Said transmission output is then transmitted back to the evaluator station, which then controls its own-transmission output accordingly.

It is assured in this way that the transmission output of the electrodes and of the evaluator station (including, if necessary, the HF-energy supply) is adapted in each case in such a way that the signal level will not fall-short of or exceed certain lower and upper limits in the receiver and in the transmitter. The radiated transmission output is always adjusted by such control processes to the minimum required at the given time in order to receive data with adequate quality, or to optimally operate the electronic units of the electrodes. The transmission output can be adjusted step by step or continuously. This provides the evaluator station with the capability, among other things, to detect whether a signal change is caused by variations in the supply voltage, in the transmission output (with changes in distance), or by a change in the sensor output signal, which is important, for example in connection with amplitude modulation.

Alternatively, instead of the transmission output, the control unit can also control the redundance in the data flow if the bit error rate exceeds a preset threshold value.

A further development also consists in arranging in the electrodes a shutoff unit. When a preset maximum value for the required transmitting output of an electrode (and also of the evaluator unit, if need be) is exceeded, the respective electrode is temporarily automatically deactivated by means of the shutoff unit, the data transmission or recording of the measured values is temporarily interrupted in this way. The evaluator unit then adjusts itself only to the remaining electrodes and may emit an alarm signal depending on the adjustment. The required transmission outputs may be determined, for example by the control unit or by the reference elements in the respective electrodes. Said procedure can be particularly desirable when an infant, during monitoring, is turning, for example from the back to the belly and comes to rest on one or several electrodes. A possible biological stress due to HF-radiation is excluded in this way. The temporary shutoff of electrodes basically can be controlled also by integrated position and/or inclination sensors.

The device according to the invention permits the patient to move freely during the recording of the measured values because such patient is no longer connected to an evaluator station via troublesome cables. When batteries or accumulators are used, such patient may even leave the room for a certain amount of time, especially if the individual electrodes have a data memory. Especially in hospitals, the mobility of the patient can be increased further if the evaluator station(s) comprise a plurality of global transmission or receiving antennas (arranged, for example, in different rooms and hallways). Advantages of the device according to the invention are seen also in the field of emergency medicine. A victim of an accident can be fitted with the electrodes already at the site of the accident, and their signals are then continuously transmitted to evaluator stations (ES), first to the ES in the ambulance and then to any desired ES in the hospital. The correct code for the electrodes or set-of electrodes can be transmitted to the evaluator station in the hospital, for example by means of chip cards or magnetic plug-in cards.

By equipping the evaluator station with an accumulator, infant monitoring can be carried out also "on the road", for example in the baby carriage or while driving in an automobile, especially if such station has a removable monitoring module.

For monitoring patients, it is particularly possible that only a limited number of electrodes connected to the patient receives sensor data and transmits same to the evaluator station. If irregularities or abnormalities occur, the evaluator station can then connect additional electrodes or sensors by deactivating the shutoff unit.

Furthermore, the energy consumption of switched-off electrodes can be reduced in that such electrodes are capable of receiving (for an activation by the ES) and/or measuring (for example for the integrated (position) sensors) only at certain time intervals.

An additional feature of the invention consists in that identification units can be arranged in the electrodes. By allocating certain identification codes-patient code (for a set of electrodes) as well as electrode or sensor code—the evaluator station is then capable of simultaneously supplying several patients in a room, such patients each having a great number of various electrodes, and to evaluate the data and to allocate electrodes or sensors to the respective patients. This is realized in a way such that the electrode for the identification unit has a control logic, as well as a memory for storing the identification codes. The identification unit of the electrodes is preferably programmed by high-frequency radio transmission of control characters and of the respective identification code from the programming unit of the evaluator station to the respective electrodes. A further development comprises the arrangement of (pressure) switches in the electrodes as programming lockouts, particularly for preventing unintentional reprogramming.

A preferred further development of the device according to the invention particularly for long-term monitoring (for example for monitoring infants) is designed in such a way that the electrodes are already equipped with an evaluator unit (with memory). The data transmission can then take place from the electrodes to the evaluator station temporarily (for example by packets) and/or already processed, if need be (following the reduction of redundant information), or, if necessary, only in the event of irregularities, or when medical abnormalities occur. Irregularities and abnormalities are detected, for example in that the signals are outside certain preset tolerance limits, or in that they deviate more strongly from the values of preceding measurements, which are stored in the (intermediate) memory. The tolerance limits are preferably transmitted by the evaluator station to the electrode and stored in the latter.

The evaluator station (and also the electrodes, if need be) preferably contain(s) a control unit for the various functional units. In the presence of malfunctions (for example: connection to the electrode is defective), the evaluator station can then emit a sound and/or visual warning signal. In addition, it is possible to duplicate critical or important components of the evaluator station (and/or of the electrodes), or to have them present as multiple units. Possible malfunctions can be reduced in this way. Furthermore, the evaluator station and/or the electrodes can be provided with protective devices, for example for preventing antenna overvoltages.

A preferred embodiment consists in the arrangement of control sensors in the electrodes for error detection. A possible error cause, for example, consists in that a sensor no longer receives any measuring signals, or falsified measuring signals because the electrode has become detached from the skin. Temperature, impedance (measurement of the transient resistance) or spacing sensors are suitable for the control. In this way, a malfunction of the electrodes can be distinguished from possible medical abnormalities or irregularities and thus assure a correct recording of the data, or prevent error alarms (especially in connection with home monitoring).

By means of a status unit in connection with the evaluator station it is possible to adjust which electrodes or sensors are to be used for the medical diagnosis or monitoring. In addition the status unit of the evaluator station can additionally assume control functions, for example by automatically detecting (for example by means of the control sensors arranged in the electrodes, or through the reference element, which measures the supply voltage) whether the electrodes are correctly connected to the body at the start of the medical diagnosis or monitoring. Alternatively or additionally, the electrodes can be equipped with an ON/OFF switch for the activation.

Ideally, all electronic components of the electrodes such as the sensor unit, the sensor control unit, the energy supply unit (except for the accumulator) etc. are designed as integrated circuits and realized on one single chip (electrode chip). In particular, the electrode chips can be realized as ASIC's (application-specific integrated circuit), or in the form of ASIS's (application-specific intelligent sensor).

ASIC's include, among other things, microprocessors (with user programs in the program memory), circuits with programmable wiring (for example cutting through conducting paths by burning, or through application-specific manufacture of the last mask), and (gate, transistor) arrays. Array circuits represent chips manufactured in standardized ways, whose individual components (e.g. sensors, operation amplifiers, transistors, diodes, etc.) are not connected, and thus unwired. The individual elements are arranged in matrix-form in rows or columns, whereby intermediate spaces are left clear for the wiring. The connections of the individual elements in one or several metallization planes are produced according to the requirements. By using more modern C-MOS technologies (e.g. 0.1 µm technology), the structural dimensions can be highly reduced and the current consumption of the semiconductor components can be kept low. Particularly in connection with ASIS's on a wafer (preferably silicon or GaAs), the chips with the elementary sensors and suitable electronic circuit structures for the control electronics are manufactured with microelectric process steps (for example thermal oxidation, diffusion, ion implantation, metallization, passivation), as well as possibly processes of micromechanics, thin-layer, or thick-layer technology. The individual chips are subsequently finished in the metallization plane depending on the application. The electrode chips designed as type ASIS or ASICS thus offer the advantage of a rational semiconductor manufacture in spite of varied and different application specifications.

Preferably, the electronic components of the electrodes and evaluator station are realized by means of digital circuit technology. The digital circuit technology satisfies in an ideal way the requirements with respect to integration capability, stability and programmability. Ideally, the evaluator unit of the evaluator station (ES) and/or of the electrodes, as well as the sensor control and transmission control and frequency generation units are realized as microprocessors. However, for the determination of high transmission frequencies, it is necessary the design the receiving and transmitting units in part based on the analog technology.

For reducing the chip size further, preferably the two-side technology or the 3D-integration is used. With the two-side technology, the front and back sides of the chips are used for integrating the individual semiconductor components. It is possible, for example, to arrange the individual elementary sensors in the back side of the chips, and the signal processing and transmitting/receiving units, as well as the evaluating and storing units, if necessary, in the front side of the chips. The electrode chip may be designed also based on the hybrid technology, among others. In connection with the latter, the component is divided in different units such as, for example in a sensor assembly, transceiver assembly, etc.

Preferred embodiments of the (bio)sensors are discussed in the following in greater detail. For reducing the number of electrodes, preferably several sensors are arranged in one electrode.

The biophysical recording of measured values is carried out, on the one hand, by means of semiconductor sensors, which are based on the transistor (field effect or bipolar type), diode or capacitor principle. Examples of such sensors are:

The ISFET, which is structured similar to the MIS-field effect transistor; the metallic gate electrode (control electrode) is, with the ISFET, replaced by an ion-sensitive diaphragm. As diaphragm materials of a sensitive nature, use if made, for example of the following materials: $Sio_xN_y$, $Si_3N_4$, $Al_2O_3$, $Ta_2O_5$, $ZrO_2$, AgCl, AgBr, and various polymers, as well as biochemically active materials (enzymes).

The MOS gas sensor with (catalytic) metal gate electrode (e.g. palladium, platinum) reacts to hydrogen and, with geometrically structured gate electrodes, to other gases (transverse sensitivity). By using integrated (porous) filter layers it is possible to influence the cross sensitivity and thus the response behavior. With circuits of MOS gas sensors that are connected in parallel or in series it is possible to obtain distinct quality improvements and a superior response behavior.

The barrier-layer temperature sensor, in which the temperature dependency of p-n junctions in semiconductor components is used for measuring the temperature. Preferably, for this purpose, two identical transistors are operated in a differentiating network at the same temperature with different collector currents (measuring accuracy about 0.1° C.).

Photodiodes, especially the p-i-n photodiode, as well as phototransistors.

One alternative consists in realizing the sensors (and circuits) by means of thin-layer technology by applying thin inorganic or organic layers (films) to an insulating carrier material (substrate). The measuring principle of such sensors is based on the change in the electrical properties (e.g. electric resistance) of the thin layer under the influence of the external quantity to be measured. The application of this technology permits integrating a great number of elementary sensors with circuits on one chip, e.g. based on the hybrid technology. In connection with the thin-layer technology, vacuum processes are used for producing (by vapor deposition, application by atomization, or chemical deposition) thin metal, insulator or semiconductor layers on ceramic material, glass or plastic substrates, with layer thicknesses of less than 1 µm. As layer materials, preferably metal layers (e.g. aluminum, chromium) are used for conductors (conductor paths) and electrode pins, and for resistor layers preferably, for example, NiCr and tantalum, and for insulating layers preferably $SiO_2$, $Si_3N_4$, AlAs (for the GaAs-technology), and $Ta_2O_5$. The following can be produced as sensors with application of the thin-layer technology:

Temperature-dependent resistor layers made, for example of platinum, gold, nickel, copper and iridium (resistance thermometer; and possibly thermoelements (Seebeck effect);

light-sensitive layers, for example made of CdS, PbSe, Si, etc.;

moisture-sensitive layers: the sensor contains electrodes engaging each other in a toothed way like a comb, such mating electrodes being protected against the moisture-sensitive layer/layer sequence. For realizing the moisture-sensitive layer it is possible to use materials such as polymeric plastics, metal oxides, and porous ceramic materials;

gas-sensitive layers such as, for example, semiconducting metal oxide layers ($SnO_2$, $Fe_2O_3$), particularly for detecting $CO_2$;

magnetoresistive layers such as, for example Ni—Fe-alloys, as well as pressure-sensitive resistance layers such as strain gauges consisting of metallic film resistors (e.g. NiCr, CrSi and TaNi layers or foils, or of semiconductor layers. The pressure is measured in this connection through a change in the electric resistance; with metal strain gauges through a deformation; and with the more sensitive semiconductor-type strain gauges through the piezoresistive effect.

The thin-layer sensors particularly include also the SSW-sensors (sound surface wave). SSW-sensors belong to the SSW-components whose function is based on the stimulation of mechanical vibrations on the surface of piezoelectric solids or layer structures when an electric voltage is applied to a metallic converter (IDC=interdigital converter) with mating finger structures. The SSW-sensor, when converting the sound wave into an electric signal, makes use of the electroresistive effect, which represents the reversal of the piezoelectric effect. The surface wave propagating between two IDC's is freely accessible and subjected to different biophysical quantities. Its propagation property (propagation rate and attenuation) is dependent upon, for example the gas concentration (by means of selectively absorbing layers), the moisture and the temperature of the surrounding medium directly on the surface of the substrate. With the help of these sensors it is possible, therefore to realize different biophysical sensors, particularly gas sensors, temperature sensors, and moisture sensors. The great advantage of the SSW-sensors is the direct conversion of the measured biophysical quantity into a frequency and the frequency-analogous interface connected therewith. This results in relatively good immunity to interference, high reliability, as well as simple digitalization, because a simple frequency counter can be used instead of an analog-to-digital converter.

Since the substrate can be selected largely independently of the type of sensor layer used, the substrate and the sensor layer can be optimized independently of one another with respect to their specific properties, and a complex sensor system can be realized in this way. The thin-layer sensor technology and the semiconductor sensor technology are consequently fully process-compatible.

Basically, the thick-layer technology can be used for the manufacture of the electrode chips or of the sensors as well, for example for realizing the structure of superset or hybrid-integrated circuits.

For monitoring the breathing, acceleration sensors or also motion sensors) consisting of one or a plurality of semiconductor components with inert mass are used, on the one hand, by measuring the up and down motion of the thoracic cage or of the abdomen. These sensors are considerably more sensitive and reliable than the conventional "air cushion electrodes", and, furthermore, integratable.

The breathing can be controlled—also via a spacing sensor, which is integrated in an electrode arranged within the abdominal region. The spacing between the electrode and the evaluator station, which varies with the respiratory activity, can be determined in this connection, for example based on the difference in running time of the signals between the electrode and the evaluator station. The antenna of the evaluator station is, for this purpose, preferably mounted directly above the sleeping patient or the infant to be monitored. For control purposes it is possible to use additional spacing sensors, which are integrated in reference electrodes (mounted in sites that do not sensitively react to breathing motions such as, for example, on the head, arm, leg, etc.), or in other electrodes. It is possible in this way to distinguish movements of the entire body from breathing motions.

Alternatives to monitoring of the breathing by means of acceleration or spacing sensors consist in the use of temperature, gas ($CO_2$ or $O_2$) or air humidity sensors, which are attached near the mouth and nose (preferably between the two).

The oxygen can be measured, for example by means of a Clark-cell. For this purpose, a micromechanical, spiral-shaped groove is etched, for example in an Si-chip or Si-wafer. A silver anode is produced by vapor deposition on the bottom of the groove, and a silver cathode between the grooves. The groove is filled with a polymer, which is impregnated with common salt solution, and finally covered with the diaphragm, the latter being permeable to oxygen. When a dc voltage (abt. 0.8 V) is applied to the electrodes, an electrolyse reaction occurs, which supplies a current proportional to the oxygen concentration.

$CO_2$ is detected, for example by means of an ISFET, whose ion-sensitive diaphragm contains a water-impregnated layer. In this connection, the $CO_2$ diffusing into the water-impregnated layer leads to a chemical reaction with pH-shift.

The impedance or potential measurement, for example for the EKG or EEG signals, is carried out by means of measurement amplifiers consisting of difference operation amplifiers (with installed filters). Basically, also 3 and more tapping points (hereinafter referred to as electrode pins) can be arranged in one electrode. One electrode pin can be used in this connection for the reference value.

For measuring potential differences or impedances, a galvanic connection has to be present between the individual tapping points. Therefore, without a galvanic connection, it is possible only to determine the impedance values between the individual electrode pins in an electrode. Since the spacing between such electrode pins can be selected relatively small (up to about 1 cm; ideally 3 to 5 cm), it is possible in this way to monitor action voltages in small regions because the transmission takes place only over a small distance, which permits more sensitive measurements. In order to determine impedances or action potentials over greater distances, i.e., for example between two electrodes, such electrodes are galvanically connected with each other by means of a plug connection (for this purpose, the galvanically coupled electrodes have to be equipped only with the required electrode pins and, if need be, measurement amplifiers, but must not have their own transmitting, receiving, energy supply units, etc.).

Integrating two or more electrode pins in one electrode considerably simplifies the handling. In addition, the arrangement due to the integration of control sensors, permits a significantly better error diagnosis, for example in the event of incorrect mounting. Preferably, the sensor has an oblong shape (with two electrode pins) or the shape of a cloverleaf (with 3 or 4 electrode pins), which assures that with a small electrode surface, the spacing between the individual electrode pins or tapping points will not be too small, which would lead to measuring errors especially at high skin/electrode transition resistance.

The transition from the ion conduction of the body to the electrode line of the (EKG/EEG) lead connections takes place at the electric transition between the (EKG/EEG) electrode pins and the skin of the patient.

This generates a galvanoelectric dc voltage which, due to irregularities of the skin, can assume different values, and which effects a galvanoelectric dc voltage between two (EKG/EEG) electrode pins. Said voltage has to be suppressed in the processing of the signal because it is significantly higher than the useful signal. Furthermore, as little current as possible should flow via the (EKG/EEG) electrode pins because such flow changes the chemical composition of the skin and causes polarization voltages that may vary highly in terms of time.

Therefore, the input currents have to be low and the input amplifier has to have a high input impedance. These conditions are ideally satisfied by operation amplifiers or measurement amplifiers based on the former.

It is notable in connection with impedance and potential measurements that conventional multiplexers are not capable of well-processing signals in the mv-range with a high dc voltage component. Therefore, for processing such signals, the dc voltage is suppressed by means of filters. Multiplexing of the sensor signals then takes place following the input amplification. Measuring the action potential by means of measurement amplifiers has the advantage that suppression of the dc voltage by filters (high-pass or bandpass filters) can be effected already directly in the measurement amplifier.

For temperature measurements, it is possible to use—in addition to the aforementioned sensors—also propagation resistance sensors, polysilicon temperature sensors (preferably based on the thin-layer technology), and basically also thermoelements. A contactless temperature measurement of the surface of the skin is basically possible as well; the temperature is detected, for example via the emitted heat radiation (infrared, remote infrared) of the body. With propagation resistance sensors, which have a high long-term stability, the specific resistance of semiconductors is measured according to the single-tip method. The propagation resistor preferably consists of a monocrystalline Si-crystal (e.g. with a lateral edge length l of about 0.5 mm and a thickness h of 0.2 mm) and has on the top side an etched contact hole with a diameter d ($\ll$h, l) of about 20 µm, from which a contact is produced by a strong doping ($n^+$) and application of metallization layers. The resistance R between a rearward metal contact and the metallization contact then only is still dependent upon the temperature-dependent specific semiconductor resistance p of the (n–) doped silicon (R=p/2d).

Position sensors for the determination of the (sleeping) position of the patient (for example belly, back or side position) are preferably realized by magnetic field sensors. Magnetic field sensors contain, for example a Hall element consisting of a (thin, long stretched-out) metal platelet, or a silicon or GaAs semiconductor platelet. For the determination of the position, a constant current is impressed into the Hall element, and the Hall voltage is evaluated as a function of the magnetic flow or the vertical component of the outer magnetic field of the earth. By arranging three Hall elements in the sensor or electrode, such elements being arranged vertically relative to each other, it is then possible to determine the exact position (belly, back or side position) of the patient.

An alternative in the use of inclination sensors, which is many cases operate according to the capacitive measuring principle. Capacitive inclination sensors consist of a microstructured measuring cell, which is filled with liquid an inert gas. In this connection, the two plates of a capacitor (or of a plurality of capacitors) are more or less covered by the liquid dielectric depending on the inclination. Turning of the sensor results in a change in capacity that is proportional to the angle. Basically, the position can be determined via micromechanical sensors as well.

Control sensors are used especially for avoiding false alarms or falsified measured values. Such sensors can be realized, for example in the form of spacing sensors (ultrasound or radiation emitters and transmitters for determining the distance between the electrode and the skin), impedance sensors (measurement of the transition resistance between the electrode and the skin), temperature sensors (sensor measures the temperature of 36° C. if the electrode is suitably attached), moisture sensors, or reference sensors.

For the determination of the value of oxygen saturation ($O_2$) in the blood, transmission or reflection measurements are carried out. Preferably IR radiation emitters and receivers (diodes) are used for these measurements. IR emitters and receivers are arranged in this connection on the same or opposite sides of parts of the body (fingers, toes, palm or back of the hands) with high blood circulation (also on thin parts in connection with transition measurements).

Moisture sensors are preferably realized in the form of impedance sensors (operation amplifiers) or ISFET's, which determine the sweat content or the pH (ion concentration of NaCl) on the skin.

Usefully, the evaluator station contains a calibration unit (with memory) for the sensors, in particular for the temperatures, gas, ion-sensitive and Hall sensors. Basically, such a calibration unit can be arranged in the respective electrodes as well.

The radio transmission of the digitalized and coded sensor data is effected by the digital modulation (rekeying) of a sinusiodal carrier signal, in connection with which shifting takes place between discrete (e.g. two or four) wave shapes, or by means of discrete pulse modulation methods. The modulation or demodulation can take place directly in this connection (i.e. at the transmission frequency), or also indirectly (with an intermediate frequency), in which case, however, changing (via mixers) to the transmission frequency is necessary.

In connection with the digital carrier frequency technology, either the amplitude, preferably, however, the frequency (FSK=frequency shift keying), or the phase (PSK)—as particularly with the GMSK=Gaussian minimum shift keying—is varied (modulated), or a combination from the three methods is used.

For the discrete pulse modulation (basic band transmission), particularly the PCM-method (pulse code modulation) or the DM (delta modulation) method is considered. These methods are preferably used for the optical transmission of the data (e.g. in the IR-range by means of semiconductor diodes). In this connection, by scanning with quantized amplitudes, a change of analog (sensor) signals into coded digital signals takes place, namely mostly in sequences of binary pulses with the values 0 or 1. Possible are 8—for example with compounding—, but also 10 or higher-digit (linear) code words are possible with one or several parity bits. Coding is carried out, for example according to the Manchester-method.

For superior exploitation of the transmission channels, i.e., in order to be able to transmit the sensor data and the data of the evaluator station independently and simultaneously, the individual signals of the electrodes or sensors and of the evaluator station are preferably additionally processed prior to the transmission by a multiplexer (line transmission). Among the multiplex-methods, especially the TDMA (time division multiple access) process, the FDMA (frequency division MA) method, and the CDMA (code division MA) method are of interest.

With the TDMA-method, message signals are transmitted in blocks of data in a time-interleaved arrangement in a cyclic sequence. With the PCM, for example, this is possible because the pulses have a short duration, so that scanning samples of other input signals can be inserted in the intermediate spaces. With the FDMA method, the transmission medium is divided in N identically sized frequency bands (e.g. with N or N/2 transmitters). By modulation with staggered carrier frequencies, the basic bands of the primary signals are shifted in this way to higher frequency positions, in a way such that they come to rest next to each other on the frequency scale.

With the CDMA-method, a distinction can be made in this connection between the "frequency hogging" and the "direct-frequency" coding. With the frequency hopping, several frequency (part) bands are available for the transmission. The message to be transmitted is divided in packets of the same length, which are transmitted one after the other on different part bands. In this way, a noise pulse generator cannot simultaneously interfere with all frequencies, so that only a few packets are disturbed by such a generator. Due to sufficiently high redundancy, the entire message will then reach the receiver with a good quality in spite of the interference. With direct sequence or also pseudo-noise coding, the message is highly stretched by bits in terms of time before it is transmitted, and modulated with a pseudo-random binary sequence. A receiver knowing the binary sequence can extract the useful signal again from the pseudo-noise. The separation of the signals is assured by the selection of orthogonal code sequences. This permits, on the one hand, a parallel transmission of different messages on one band; on the other hand, this method is relatively insensitive to wideband and narrowband interferences.

The space-division multiplex method offers another possibility for data transmission. In this case, the evaluator station is equipped with a plurality of transmitting/receiving antennas, which each are directed at different patients to be monitored. Said method, furthermore, has the advantage that the antennas can be arranged relatively close to the patient (e.g. directly above the patient's bed), which permits reducing the transmission power. Especially in connection with directional antennas, the antenna can be equipped with an additional control unit and a driving motor, such unit and motor aligning or adjusting the antenna in such a way that the transmitting/receiving adjustment is always optimal. This method basically can be used also in connection with a great number of electrodes attached to the patient. Especially with very large systems, for example in hospitals, several evaluator stations each having several antennas can be interlinked via cables or radio transmission. The individual sets of electrodes will always respond to the most suitable evaluator station or antenna (e.g. to the closest one), and when the patient is moving, will be handed-over to the next ES, if need be (handover). For reducing interferences, the individual evaluator stations are preferably operated on different frequency bands.

Depending on the complexity of the data transmission methods, transmission control units are arranged in the electrodes. Preferably the evaluator station has a master transmission control unit and controls the transmission control units of the electrodes via signalizing data (synchronization). In this way, the evaluator station prevents collisions in the data transmission of different electrodes.

So that in the data transmission, the receiver is capable of scanning the received signals at the correct points in time in order to be capable of recognizing the individual bits correctly, a synchronous operation between the transmitter and the receiver is useful and necessary (synchronous data transmission). For this purpose, the evaluator station preferably contains a synchronizing unit which, as the reference cycle clock generator, controls the clock generators of all nodal points of the network, i.e., of the electrodes by means of synchronization characters and/or via a reference timing frequency, for example according to the master slave method, and in this way assures the frequency, clock, base and/or frame synchronization (TDMA). In particular, the high frequency (HF) for the energy supply can be used as the reference timing frequency. It is possible also to use the demodulated signal for the clock recovery, among other things.

It is basically possible also that the cycles of the individual electrodes do not correspond with the one of the evaluator station (ES)(asynchronous operation), or slightly deviate from the cycle of the ES within preset limit values (plesiochronous operation).

If, for example, one electrode has a slightly higher clock pulse frequency than the evaluator station, the ES may occasionally be incapable to read a bit; reversely, the electrode will occasionally read a bit twice. This error can be compensated, for example through the use of padding methods, i.e., through the use of bits that do not carry any useful information. An alternative consists in that the system accepts an occasional slip. By using slip controls in the receivers it is particularly possible to prevent the system from losing its frame synchronization in spite of slip, for example in that a shift takes place by a whole frame, and not only by one bit width. Therefore, the requirements with respect to synchronization between the electrodes and the evaluator station can be low, comparatively speaking.

Suitable for the transmission is particularly also the subdivision of the signals (to be transmitted) in packets, whereby each packet is provided with suitable addressing, code protection etc. (packet transmission). One packet comprises, for example start, stop, control and synchronization bits, the address of the transmitter and of the receiver, a test code, if necessary, as well as the useful information.

In the simplest case, the data are transmitted by the simplex method, i.e., from the electrodes to the evaluator station, and without acknowledgement and reception confirmation. However, the half-duplex (in both directions, but not simultaneously) or the full-duplex operation is preferably used for the data transmission. With both of said methods, the evaluator station may both confirm the reception of the data and also transmit command sequences to the individual electrodes.

Basically random-oriented and also reservation methods are available for the channel access.

The random-based methods include particularly the ALOHA-, CSMA—(carrier sense multiple access) and CSMA-CD—(CSMA with collision detection) methods, which are not discussed here in greater detail because they are of secondary importance to the device according to the invention. In connection with the reservation methods, the physical channel is divided by a time period (TDMA), a frequency (FDMA), or a code (CDMA). The channel access can take place also priority-oriented, i.e., according to a preset priority stage of the individual electrodes. The fixed allocation of transmission rights is possible only with knowledge of the number of electrodes or electrode sets that may transmit simultaneously.

For safeguarding the transmission quality it is advantageous, furthermore, to carry out the transmission according to the (code-independent) HDLC-method (high level data link control). In connection with said method, not each block is individually acknowledged after it has been transmitted, but several blocks are transmitted in one direction one after the other. The receiver (e.g. the evaluator station) can insert the acknowledgement in own data blocks, which are transmitted in the reverse direction (e.g. to the respective electrodes).

For reducing transmission errors, additional redundancy can be incorporated in the message sequence to be transmitted (channel coding). Deterministic codes (such as, for example, block codes, recurrent codes) and also stochastic codes can be used in this connection. An error correction unit in the evaluator station and/or in the electrodes will then execute, for example a direct error correction at 1-bit transmission errors (FEC=forward error correction), so that a repeat request for repeating the data transmission can be omitted.

The data to be transmitted can be coded by a secret code for special applications. For this purpose, the signal processing units of the electrodes and of the evaluator station are equipped with coding and decoding units. Said units are preferably arranged in the encoders and decoders, respectively.

For increasing the reliability of the data transmission, training sequence units or equalizers may be arranged especially in the electrodes and/or evaluator station. A training sequence unit in the electrode generates a test code (character sequence), which is specified between the transmitter and the receiver, and transmits said test code to the evaluator station at defined times. The test code also may consist of, for example the identification code of the individual electrodes, or contain said code. With the packet or time-slot operation, the test code is preferably arranged in the center of each packet or time-slot. The equalizer in the evaluator station compares the received test code with the specified one, and determines the algorithm for recovering the transmitted data. In the event of distortions or trouble such as due to multiple reflections, diffraction and interferences due to the absence of sight contact between the receiving antenna of the evaluator station and the electrodes (patient turned away, dressed or under the bed blanket), the receiver can then equalize the transmission. The equalizer and the training sequence unit also may be arranged in the electrodes or the evaluator station alternatively or additionally. The use of test codes is particularly useful if the transmission distances are greater or if the transmission frequencies or bit rates are very high.

A preferred further development consists in the use of nesting/denesting units. For this purpose, individual bits of a data block are time-interleaved (scrambling) and divided in a number of sub-blocks. Especially in connection with the TDMA-method, such sub-blocks can be divided in different data bursts. On the receiving side, burst errors lead to 1-bit errors of the unscrambled data and may be eliminated by the error correction unit, so that data transmission errors are thus reduced.

BRIEF DESCRIPTION OF THE DRAWINGS

Preferred embodiments of the device according to the invention are explained in greater detail in the following by reference to the attached drawings, in which:

FIG. 2a shows a cross sectional representation of an electrode with a plurality of sensors according to FIG. 1;

FIG. 2b shows a cross sectional representation of an alternative electrode with a plurality of sensors;

FIG 2d shows a plan view of the electrode shown in FIG. 2a;

FIG. 2e shows a plan view of the electrode shown in FIG. 2b;

FIG. 4a shows an electrode for absorption measurements;

FIG. 4b shows a transcutaneous oxygen ($tcpO_2$) and carbon dioxide ($tcpCO_2$) electrode;

FIG. 5 shows a transcutaneous oxygen ($tcpO_2$) and carbon dioxide ($tcpCO_2$) electrode;

FIG. 6 shows a hand electrode for an infant;

FIG. 1 shows the basic schematic structure of the device according to the invention. The device contains as components an evaluator station (1), as well as one or a plurality of electrodes (2a to 2f), which are arranged on one (or a number of) patient(s). In the example explained here, the data are to be exchanged between the valuator station and the various electrodes according to the TDMA-method with PSK-modulation. Without limiting the general idea of the invention, the individual electrodes within a set of electrodes (i.e., for a certain patient), furthermore, are to have the same transmission frequencies, whereby the transmission is to take place in the doublex operation with two separate frequency bands in the 1 GH2-range (with less complex systems, e.g. for the home monitoring of infants, with a highly limited or specified number of electrodes, the frequency multiplex method can be used as well).

Figure 1:
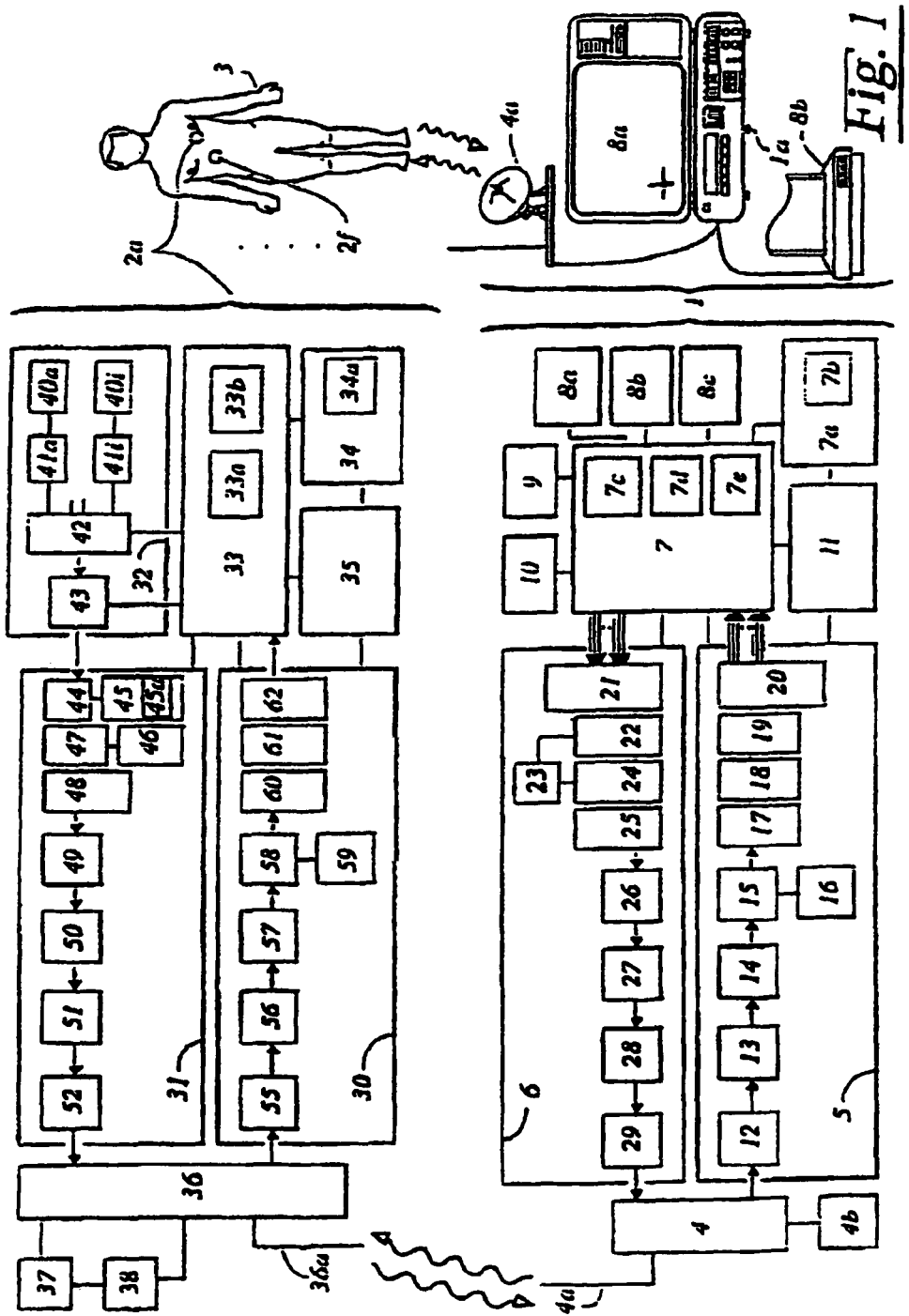
FIG. 1 shows a schematic structure of the device according to the invention.

With multiple access in the time multiplex, the electrodes and the evaluator station periodically transmit pulse bundles (bursts). For synchronization, the bursts are combined in frames. The transmission times of the pulse bundles (e.g. data bursts) transmitted by the various electrodes are shifted against each other in terms of time in such a way that the busts are lined up at the input of the various receivers (e.g. of the evaluator station) with as few gaps as possible without, however, overlapping one another. This is achieved, for example in that each electrode transmits its burst in reference to a reference burst, which is transmitted by the evaluator station, and controls and corrects the transmission phase with the help of the reference bust. In particular, in the presence of greater distances, the running time of the signal s between the electrode and the evaluator station can be taken into account in connection with the transmission phase the electrode as well. In addition to the transmitted sensor or useful data, each data burst also contains a preamble consisting of the synchronizing header, the start-of-message identifier of the burst, if necessary sender addresses, and additional system-internal signalizing the, if need be. The synchronizing header is a preset code sequence permitting a rapid synchronization of the carrier, cycle and frame (additional synchronization can take place via separate synchronization bursts). The start identifiers of the bursts indicate at which point of the header the receiver has synchronized. Dummy bursts are used when no useful data are transmitted. The first access preferably takes place according to radomOoriented (e.g. ALOHA) or also according to priority-oriented methods.

The evaluator station (1) shown here is equipped with a receiving and transmitting antenna (4a), a receiving/transmitting separating filter (antenna separating filter, frequency separating filter, bridge separating filter) (4), a control unit (4b)—for determining/controlling the transmission power—, a receiving unit (5), a transmitting unit (6), as well as with a data processing or evaluating unit (7) with associated display (8a), printer (8b), storage (8c) and alarm (10) units. Additional components are the frequency generation unit (11) as well as the transmission control unit (7a) with the sequencing control (7b). The evaluator unit (7) contains a status unit (7c), which controls the selection of the patient, of the electrodes, as well as of the sensors contained in the latter. Based on such selection it is determined to which sensor a subsequent command is addressed. For detecting and minimizing transmission errors, provision is made in the evaluator station (7) for an error diagnosis and correction unit (7d). The latter uses redundant information in the transmission in order to be capable of eliminating errors. In order to permit a simple calibration of the sensors (40a . . . 49i) of the electrode (2), provision is made for a calibration unit (7e). The electrode is subjected to a fixed standard condition, from which the signals of the sensors (40a . . . 40i) to be expected are known. The calibration unit (7e) adjusts internal parameters of the electrode (2) such as, for example amplification factors or offsets, to such an extent that the sensors (40a . . . 40i) supply the expected signals. The receiving unit (5) or transmitting unit (6) substantially consists of a signal conversion unit (12-16, and 26-29, respectively), as well as of a signal processing unit (17-20 and 21-25, respectively) (this applies analogously to the electrodes).

The signal conversion unit for the receiving unit (5) contains a high-frequency amplifier (12) with synchronizable bandpass filters (for preselecting the transmission frequency of the individual electrodes), a mixer unit (13), a low-frequency (LF) amplifier with filters (14), as well as a demodulator (15). The mixer unit (13) may, in this connection, comprises a plurality of intermediate-frequency mixing stages (with the respective filter and amplifier stages), and, via one (or several) oscillator(s) in the frequency generator (11) (frequency synthesizer), converts the high frequency signals received (in the GHz-range) into the basic band (or an intermediate-frequency band). In the demodulator (15), which preferably is a quadraturE modulator, the signals are finally PSK-demodulated, as well as amplified again, if necessary (not shown). A connected equalizer (16) equalizes the signals. The demodulated signals are finally processed by the burst demultiplexer (17), which executes the TDMA-deframing, the deleaving unit (18), as well as the decoding unit (19), and the digital signals are further transmitted to the evaluator unit (7). The decoding unit (19) converts the signals received into binary signals, and executes an error correction. By means of the specific identification codes, which, for example, are stored in the evaluator unit (7) or in a separate identification unit, the individual data can be assigned to the respective patients, electrodes, or sensors. Subsequently, the different electrode data can be assigned to the respective evaluator sub-units by a demultiplexer (20).

The transmitting unit (6) comprises the digital multiplexer (21), the encoding unit (22), a training sequence unit (23), the interleaving unit (24), the burst multiplexer (25) for the TDMA-framing, the (PSK) modulator (26), a low-frequency amplifier (27), the mixer (28), as well as finally the HF-transmission amplifier (29) with built-in bandpasses.

The control unit (7a) serves for controlling the transmission between the evaluator station and the electrodes, as well as for controlling the frequency generation unit (11) and the sequencing control unit (7b). The frequency generation unit (11) especially comprises also a clock unit, which supplies the various system cycles especially for the evaluator processor (7) and the TDMA frame structure. Said unit particularly serves also for frequency and cycle synchronization of the electrodes with the evaluator station. For this purpose, the carrier frequencies and the system cycle are transmitted to the individual electrodes by the evaluator station via synchronization bursts (the high frequency field received for the energy supply can be used also directly, for example for transmitting the carrier frequency, among other things).

The frequency generation unit (11) comprises, for example one or a plurality of PLL (phase-locked loop) synthesizers, which generate(s) the various carrier frequencies within the range around 1 GHz. The frequency generation unit (11) particularly supplies the various oscillator frequencies (as well as the carrier frequencies) for the mixers and modulators, and also a reference frequency, from which the individual oscillator frequencies are generated. The reference frequency can be generated in this connection by means of (temperature-compensated) quartz oscillators or synchronizable oscillators.

The evaluator station is adapted to the burst operation via the sequence control (7b), which controls the burst (de)multiplexers (16, 22), the (de)modulators (15, 26), etc. For the TDKA (de)framing, the data are fed into intermediate memories (not shown) and read in and read out at the correct points in time at the system bite rate.

For the application of a plurality of electrode sets (with different carrier frequencies), for example for simultaneously monitoring a number of patients, several receiving units (5) and transmitting units (6) are required, or one receiving and transmitting unit with a great number of (de)multiplexers, (de)modulators, amplifiers, bandpasses, etc, for the individual carrier frequencies (not shown here in the drawing).

For other transmission methods such as, for example CDMA-transmission or TDMA with frequency hopping, additional synchronization stages as well as code generators and/or frequency synthesizers for code or frequency rekeying have to be integrated in the receivers and transmitters, i.e., in the evaluator station and the electrodes.

The power supply of the evaluator station can take place in this connection via a mains transformer and/or accumulators (9). Preferably, the evaluator station contains a removable, small portable module (1a) containing the important operational units such as the antenna unit (4a), the transmitting (6) and receiving unit (5), the evaluator (7), the transmission control unit (7a), the frequency generation (11), the accumulator (9), and alarm units (10) (the latter with sound and/or visual warning signals). Thus the device can be used also outside of the home for monitoring infants, for example during automobile drives or while taking a walk.

The electrodes (2) each contain an energy supply unit (37), the receiving and transmitting antenna (36a), the latter having an antenna separating filter (36) for the transmitting and receiving operations, a transmitting unit (31), a receiving unit (30) (e.g. for synchronization, indication of the transmitting power, protocol transmission, error correction, programming and controlling), a sensor unit (34), as well as a frequency generation unit (35).

The frequency generation unit (35) particularly comprises also a clock unit for the various system cycles. The frequency generation unit (35) supplies the various oscillator frequencies (as well as the carrier frequencies) for the mixers and modulators, and also a reference frequency, from which the individual oscillator frequencies are generated. The reference frequency is preferably generated by means of a VCXO (voltage controlled crystal oscillator) reference generator, which can be retuned in a highly precise way, in order to assure the required frequency accuracy with the evaluator station. For the voltage/frequency conversion it is possible to use, for example a varactor.

The electric signals of the individual elementary sensors (40a-i) are amplified and filtered by the preamplifiers. Preferably, the sensitive input amplifiers (41a-i), for preventing over-driving, for example due to HF scatter, are equipped with protective devices, for example with a Zener diode circuit for signal limitation (not shown here). The amplified and filtered (equalized) signals are then applied to a high-speed analog multiplexes (42), which is controlled by the sensor control unit (33). The sensor control unit (33) receives the control commands from a storage unit (33a), or directly via radio transmission from the evaluator station (I). For detecting and correcting transmission errors, the electrode (2), too, has an error diagnosis and correction unit (33b), which operates in the same way as with the evaluator station (1). Then, the signals at the output of the analog multiplexer (42) are amplified again sensor-selectively by an amplifier (43), if necessary, and then applied to the analog-to-digital converter (44). By means of the identification unit (45a), the encoding unit (45) converts the analog signals into the electrode- or sensor-characteristic digital code. The coded electrode signals and the training sequence (test code) of the training sequence unit (46) are then applied to the interleaving unit (47) (the aforementioned equalizer (16) in the receiving unit (5) of the evaluator station (1) uses the training sequence for equalizing the data). The interleaved, coded sensor data are then adapted to the TDMA framing via the burst multiplexer (48), and, for modulation, fed into the (PSK) modulator unit (49). For amplification and change to the carrier frequency, the signals are applied to the mixer unit (51) via the low-frequency amplifier (50). The final HF amplifier (power amplifier) (52) with bandpasses amplifies the transmission signals and feeds the latter to the antenna (36a) by way of the transmission/receiving separating filter (36). Preferably, the sequence control (34a) controls the HF amplifier (52) in order to adjust a suitable transmission output.

The receiving unit (30) for receiving the radio and control data of the evaluator station contains the HF amplifier (55) with synchronizable bandpasses, the mixer (56), the low-frequency amplifier (57), the demodulator (58) with the equalizer (59), the burst demultiplexer (60) (for the TDMA deframing), the delacing unit (61), as well as the decoder (62). The amplified digital signals are then transmitted further, for example to the storage unit (33a) or the sensor control unit (33). The sequence control (34a) in the transmission control unit (34) especially controls the interlacing/delacing units (47; 61), the burst (de)multiplexers (48; 61), as well as the respective intermediate memories (not shown) for the TDMA-framing or TDMA-deframing.

The transmission control unit (34) is monitored by the evaluator station (1) and, when deviations from should-be values occur (e.g. of the transmitting power), receives correction instructions. The transmission control unit (34) is particularly responsible also for the frequency and cycle synchronization of the frequency generation unit (35). Preferably, the transmission control units (7a; 34) or the sequence control (7b; 34a), furthermore, contain synchronization stages (not shown in the drawing) which, on the one hand, determine the point of arrival of the bursts, and measure the channel distortion, on the other hand, in order to make the required information available to the equalizer. Said synchronization stages can be arranged also in the receiving units (5; 30). A frequency and cycle synchronization can take place particularly via the test code of the ES.

The HF-field emitted by the evaluator station is converted by the energy supply unit (37) of the electrodes into the supply voltage, and the energy supply unit stores the excess energy in an accumulator (38).

The receivers (5; 30) of the evaluator station (1) and the electrodes (2) may basically be designed in the form of straight-ahead and overlay receivers, and particularly as synchronous and quadratur receivers and Superhet's. The amplification, synchronization and selection means of the respective transmitting and receiving units, which are shown in FIG. 1 in only one box, particularly can be distributed to a number of units/stages. The individual amplifier elements in the receiving units of the evaluator station (1) and/or the electrodes (2) are controlled by an amplification control unit (AGC=automatic gain control) and monitored by the latter (not shown). The transmitting and receiving units are defined in the present specification in such a way that they contain the modulation and demodulation components.

For a digital design of the receiving units (5; 30), the signals received are converted into digital signals at intermediate frequencies ($\ll 100$ MHz), or in the basic band. For this purpose, digital-to-analog converters are integrated either in the mixing (13; 56) or in the demodulation units (15; 58). This applies analogously to the transmitting units (6 and 31) as well. The electrode units and the evaluator station are then controlled by digital microprocessors. Especially the homodyn receiver offers advantages for the monolithic integration of the entire receiver because the selection is shifted there to the basic band.

FIGS. 2a, FIGS. 2d and 2b, 2f show two typical exemplified embodiments for the design of the electrodes on a scale of about 2:1. Without limiting the basic idea of the invention, the individual electronic components of the electrodes, i.e., the elementary sensors and the sensor control, transmitting/receiving and transmission control units etc. are integrated in one signal semiconductor chip.

With the electrodes, the antenna (36a) is designed as a spiral antenna arranged in the flexible electrode covering (71). On the underside, the antenna (36a) has a reflector (35b), by which the HF power radiated from the antenna (36a) in the direction of the patient is reflected upwardly. Preferably, the spiral antenna is realized with two or four arms; only one arm is shown here for the sake of better clarity. Since radiation in the direction of the body, i.e., radiation from both sides is undesirable, a plane reflector (not shown) is mounted between the antenna and the electrode covering facing the skin, preferably with a spacing 2/4 (2=wavelength). This enhances the radiation in the desired direction of transmission; however, this is connected with a reduction of the bandwidth. Another possibility is the projection of the plane spiral antenna onto the surface of the electrode cone (conical spiral antenna).

The electrodes are fastened on the surface of the skin preferably by means of exchangeable adhesive tapes (coated with adhesive on both sides) or adhesive rings.

Some electrode designs can be basically arranged also on materials resting closely to the skin such as, for example, bracelets, pieces of garment, or mattresses, if need be. Important is only that the sensors are in adequately close contact with the body.

FIGS. 2a and 2d show a possible arrangement of the individual semiconductor elements such as the elementary sensors (40a to 40i), the sensor unit (32), an evaluator unit (74), the sensor control (33), the transmission control (34), the frequency generation (35) units, as well as the transmitting/receiving (31, 30) and the energy supply (37) units of the electrode chip (70).

FIGS. 2b and 2e show an electrode (2) with which also EKG and EEG measurements can be carried out, among others. For discharging the action potentials, two electrode pins (76) (preferably coated with silver, gold or sintered material) are arranged in the electrode (2), said pins applying the action potentials to the input of a measuring amplifier (78)—see FIG. 7 for more details—by way of shielded cables (77). For establishing a good skin contact, the electrode pins are ideally fitted on the back side with mechanical springs (79). In order to avoid moisture bridges on the skin contact side, the electrode pins are framed by a special insulating coating (89). In addition, a great number of additional sensors such as temperature (80), skin moisture (81), motion (82) and oxygen saturation (83) sensors, etc. are arranged in the electrode chip. The electrode chip (70) is realized in this connection by means of the two-layer technology, i.e., the elementary sensors (40a to 40i) are arranged on the side of the chip facing the skin, and, for example the sensor control unit (33), the transmitting/receiving (30, 31) and the frequency generation (35) units etc. are arranged on the back side. The accumulator (38) for energy storage) is, in the present embodiment, arranged above the electrode chip (70).

Figure 2F:
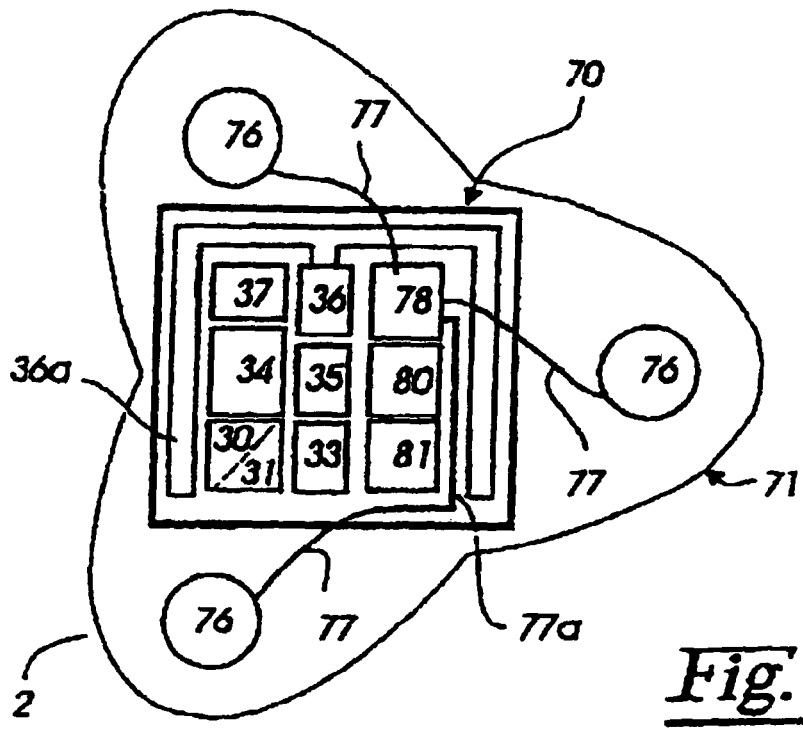
FIG. 2f shows a plan view of the electrode shown in FIG. 2c.
Figure 2C:
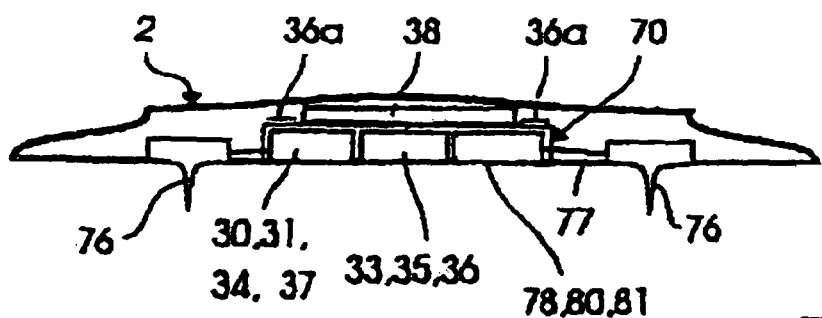
FIG. 2c shows a cross sectional representation of another alternative electrode with a plurality of sensors.

FIGS. 2c and 2f show an electrode (2) having electrode pins (76) in the form of needles. Said electrode pins (76) penetrate the skin of the patient and lead to a reduction of the transition resistance, which permit more sensitive measurements. The antenna (36a) is integrated in the electrode chip (70) for reducing the size of the electrode (2) and for superior HF-transmission.

Figure 3:
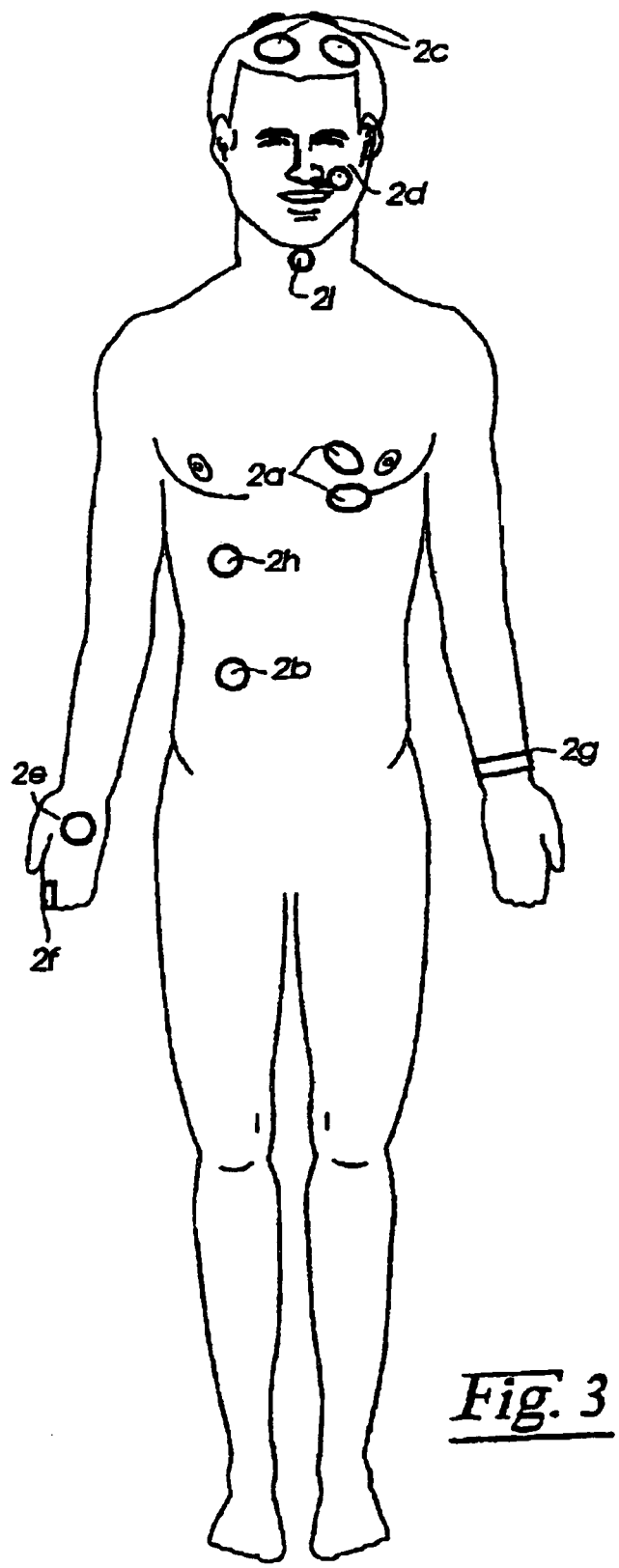
FIG. 3 shows an arrangement of the electrodes on the patient.

Various possibilities are available for the combination of sensors in one electrode; this is shown in FIG. 3 for various electrode arrangements.

The electrode(s) in the thoracic region (2a) comprise(s) EKG sensors with 2 to 4 tapping points for the action potentials (depending on the number of electrodes). The electrodes are shaped here, for example ovally or cloverleaf-like depending on the number of tapping points. One electrode is adequate for the monitoring of infants. Usefully, the electrode additionally comprises for control purposes an impedance sensor for measuring the transition resistance between the electrode and the skin. The transition resistance has an important bearing on the quality of the signals and should have values of lower than 5 to 10 kohm. In addition, the transition resistance between the individual electrode pins of an electrode is tested in order to exclude any possible short circuit (e.g. due to excessive moisture of the skin, or common salt bridge—the resistance should not be significantly lower than about 500 ohm depending on the spacing of the electrode pins.) Preferably, the evaluator station tests continuously whether said measured control values fall short of or exceed the preset upper and lower limits, especially for the purpose of avoiding false alarms. In addition, preferably an acceleration sensor is arranged in the electrode, which can measure also the cardiac activity, on the one hand, and serve as a reference measurement for the breathing, on the other hand. Further useful possibilities include the integration of a position sensor, a temperature sensor, as well as a reference sensor for the moisture measurement.

The electrode on the abdomen (2b) contains a sensor for monitoring the breathing (for example an acceleration sensor). By comparison with the data of the reference sensors (arranged, for example at 2a, 2e and/or 2f), it is possible to compensate or eliminate the influence of movements of the entire body, for example due to shocks in the carriage or during drives in the car.

The head electrode(s) (2c) contain(s) the EEG-sensors (shaped similar to the EKG-electrodes), which comprise 2 to 4 tapping points for the potential values as well. Due to the lower EEG signals (lower than the EKG signals by about a factor 1000), the head electrodes, too, comprise for control purposes impedance sensors for measuring the transition resistance. In addition, it is possible also to arrange, for example a moisture sensor between the individual electrode pins of the EEG discharge line, in order to detect in this way a short circuit or a data falsification due to excessive moisture. This procedure, of course, is possible with the EKG discharge as well.

Another possibility for the breathing control consists in the arrangement of an electrode in the facial region (2d), in particular between the mouth and the nose. With this electrode arrangement, the breathing can be measured by way of a temperature sensor. An alternative consists in monitoring the concentration of the exiting $CO_2$-content (basically also of the $O_2$ content) via a gas sensor. In addition, the respiratory activity can be monitored also by means of a moisture sensor by measuring the air humidity. With all three methods, a breathing activity is expressed by fluctuations in the ambient temperature, in the $CO_2$-content and the air humidity within the immediate proximity of the nose and mouth.

The electrode in the palm of the hand (2e), which basically can be attached also to the sole of the foot, contains a potential sensor (preferably a measuring amplifier), a capacity sensor (capacity diode), or an electrocaloric sensor (the surface charge effects a change in temperature) for measuring the electrodermal activities or the SSR. It has been found recently that electric skin phenomena occur in infants in situations causing stress for the body, which phenomena can be detected in a simple way. Such phenomena are known from the lie detector technology. The measurement of said potentials opens new possibilities for a distinction of which events (for example breathing pauses, deceleration of the heart rate) are unimportant for the organism, and which ones have to be viewed as threatening. It has been found that these signals are particularly pronounced on the palms of the hands and the soles of the feet, so that they can be registered best in said sites. Furthermore, the electrode contains a moisture sensor for measuring the moisture of the skin (perspiration) because it has been found that parallel with the SSR, stress situations cause secretion of sweat on the palms of the hands and soles of the feet. In addition, a reference sensor can be arranged in the electrodes for the breathing.

The electrode (2f) is preferably design in the form of a finger clip (see FIG. 4a). Basically, such a clip can be attached also to toes of the foot or to the bridge of the nose. It contains a sensor for measuring the oxygen saturation in the blood (pulsoximetry). The pulsoximetry takes place in this connection either by means of transmission measurement or reflection measurement with optic wavelengths between 660 nm and 940 nm. The determination of the oxygen saturation in the blood is based on the spectral absorption of the specific wavelengths on the red light and remote infrared range of hemoglobin and oxhemoglobin when such radiation penetrates the skin, muscles and tissues. For these measurements, IR light (88) or light is radiated by means of an emitting diode (e.g. Ga (AI, P) As and In (Ga)P-LED's), which penetrates the body parts with blood circulation, and which is then registered by a sensitive detector (e.g. GaAs-diode) (86). In connection with the more sensitive transmission measurements, the emitter and detector are arranged in separate units, which approximately oppose each other (as in the present exemplified embodiment). Pulsoximetry by means of reflection measurements can be carried out basically on all parts of the body (with suitable blood circulation), for example also in the thoracic region, whereby the emitter and the detector can be integrated in the same chip. Since pulsoximetric measurements react susceptibly to movements, an acceleration sensor (87) is preferably integrated in the finger clip. With the measurement of the oxygen saturation it is possible also to monitor the pulse, among other things. This is shown on the curve (K) in the cutout of FIG. 4, which represents the absorption (A) Versus time (T).

The electrode at (2g) is designed as an arm bracelet preferably made of elastic, flexible material. Especially for monitoring infants, this bracelet can be left permanently attached because it causes no inconvenience. With this bracelet it is possible to tap the pulse, for example by way of pressure sensors, and thus to monitor the cardiac activity. A combination especially with temperature and moisture sensors, or ISFET's (perspiration), as well as with acceleration sensors is suitable.

The electrode (2h), which is shown in greater detail in FIG. 5, serves for monitoring the transcutaneous oxygen ($tcpO_2$) and carbon dioxide ($tcpCO_2$) contents in the blood. These measurements, which are useful especially on infants, offer continuous information about the ability of the body to supply the tissue with oxygen, and to discharge carbon dioxide via the cardiopulmonary system. The transcutaneous $pO_2$-value permits conclusions with respect to the arterial oxygen concentration and possible changes in the heart minute volume $tcpO_2$- and $tcpCO_2$-measurements are based on the fact that an increase in the skin temperature (preferably temperatures between 38° C. and 45° C.) effects an increase in the blood circulation of the skin and of the oxygen and carbon dioxide partial pressure, and makes the skin permeable to the gas diffusion.

In the present exemplified embodiment, the individual sensors, transmitting and receiving units etc. of the electrode are not integrated in one chip. For warming up certain parts of the skin, a heating element (e.g. a heating resistor) or preferably (for preventing burns in long-term applications) a heat radiator (90) (e.g. an IR-diode) is arranged on the side of the electrode facing the skin. A suitable temperature or radiation sensor (e.g. a pyroelectric sensor) (91) as well as a control unit (92) serve for the temperature control. An oxygen sensor (93) and a carbon dioxide sensor (94) then determine the gas concentrations (95) diffusing through the surface of the skin (96). The electrode (2h) is designed in such a way that the $O_2$— and $CO_2$-molecules flow directly past the gas sensors (93, 94). The electrode is preferably open at the top because the formation of moisture between the skin and the electrode can be more easily prevented in this way. For increasing the sensitivity and for protecting the sensors, the electrode can be closed at the top and/or at the bottom by a membrane (not shown here) that is permeable to gas. Alternatively to the electrodes (2) shown in the foregoing, the electrode has a transmitting diode (98) and a receiving diode (97) for the optical transmission of the data and commands from and to the evaluator station (1).

Another monitoring of the breathing is offered by the electrode (21), which is arranged near the bronchial tube. In this connection, the noise of the respiratory flow is recorded by way of a miniaturized microphone and the flow of air is monitored in this way. The microphone can be realized in many different ways, preferably in the form of a capacitor microphone or a piezoelectric microphone.

Said electrode (21) is preferably combined with the electrode (2b) for monitoring the movement of the diaphragm. A distinction can be made in this way as to whether a central apnea (no movement of the diaphragm, no flow of air)—which apnea originates from the breathing center in the brain stem—is present, or an obstructive apnea (deglutition apnea; motion of the diaphragm, no flow of air).

For controlling and for avoiding false alarms, the individual electrodes may be equipped with additional control sensors, for example spacing sensors, which monitor the spacing between the electrode and the skin.

For infants, the fingerclip (2f) and the palm (2e) electrodes are ideally combined in one electrode. The measurement takes place in this connection preferably transversely across the palm of the hand, as shown in FIG. 6.

Figure 7A:
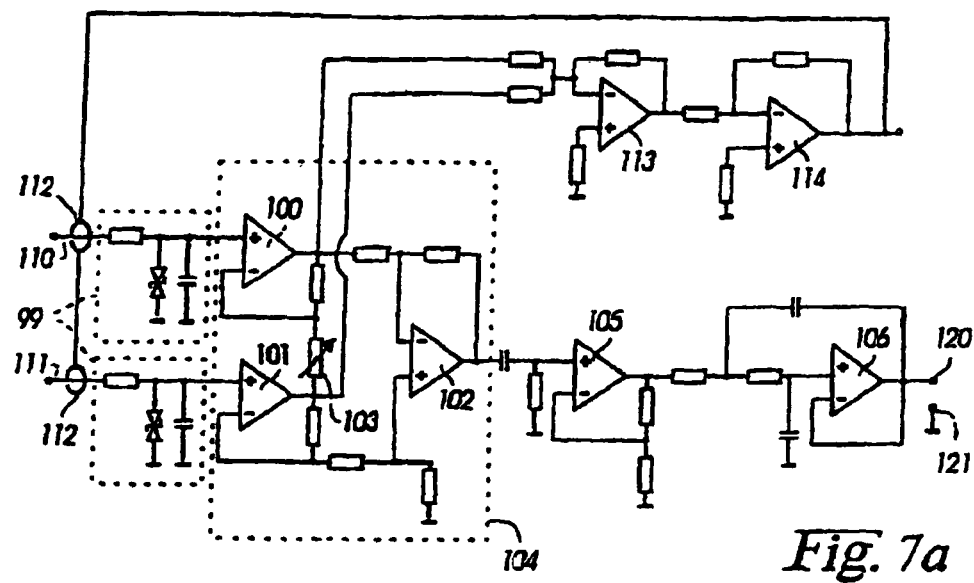
FIG. 7a shows a circuit for measuring the bio-potentials, in particular the EKG and EEG action potentials.

For measuring potential differences, it is basically possible to use one single operation amplifier. However, since the potentials to be measured have in the normal case a relatively high inner resistance, it is more useful to apply said potentials not directly to the input resistor of the subtracter. The use of impedance converters (potential sequencers) makes the operational mode of the subtracter independent of the inner resistances of the measuring potentials. FIG. 7a shows such an exemplified embodiment for an operation amplifier circuit with a protective input circuit (99)) for difference formation, preamplification and filtering. Basically, it is possible also to arrange high-pass or bandpass filters upstream of the instrument or measuring amplifier (104) for suppressing the dc potential components.

The individual EEG or EKG signals of the electrode pins are, by way of the noninverting inputs of the operation amplifiers and impedance converters (100 and 101, respectively), supplied to the operation amplifier (102), and amplified. Higher inphase suppression is obtained through partial shifting of the potential amplification to the impedance converters. The advantage of this circuit is that the difference amplification can be adjusted by varying only one single resistor (103). With the electrometer amplifier (104), an operation amplification can be saved, if need be, if the symmetry of the circuit is dispensed with.

For dc potential separation and for the suppression of low-frequency noise (10 Hz, i.e., due to body movements), the amplified signals are then applied to the operation amplifier (105), which is wired as a high-pass filter of the first order with impedance conversion.

The component (106) represents an action low-pass filter with single positive feedback, by which the high-frequency redundant noise components of the measuring signal (e.g. caused by stray pick-up) are filtered out. The amplified and filtered potential finally can be tapped off between the potential points (120) and (121). The reference potential (121) is here applied to the battery/accumulator mass (characterized by the "−"-symbols), or the mass of the energy supply unit.

With electrode pins that are spaced far apart, or with galvanic connections between the electrodes, the highly resistive input leads (110, 111) are screened for preventing capacitive noise pick-up. The present exemplified embodiment contains for this purpose an operation amplifier (113) in an adding circuit (for forming the mean value of the tapped-off signals), to which the two outputs of the operation amplifiers (100 and 101) each are connected via a resistor. Since the formation of the sum on the operation amplifier (113) is inverting, an additional operation amplifier (114) is connected downstream, via which the averaged signals are supplied to the cable screening (112).

When using 3 or more electrode pins in one electrode, additional impedance converters, operation amplifiers and high and low-pass filters are used. The connection (110), for example, can then be used as the reference point. An alternative is that an analog multiplexer (arranged, for example, between the individual impedance converters (100, 101, ...)) and the difference operation amplifier (102) successively picks up the individual bio-potentials.

Figure 7B:
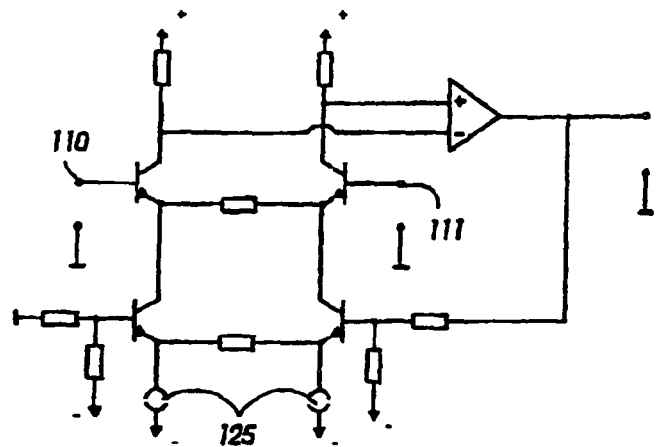
FIG. 7b shows a circuit for measuring the bio-potentials, in particular the EKG and EEG action potentials.

The module (104) shown can also be replaced by the circuit shown in FIG. 7b. As compared to the operation amplifiers/subtracters, said circuit offers the advantage that the amount of inphase suppression is here not dependent upon the pairing tolerance of the individual potential dividers. For this reason, it is possible to produce the circuit as a completely monolithically integrated circuit, whereas otherwise it is necessary to realize the critical resistors separately, using the thin-layer technology. The symbols (+) and (−) represent in this connection supply voltage (125) for a constant current source.

We claim:

1. A method for monitoring body functions of a patient comprising:
    utilizing at least one sensor with the patient, the sensor configured to detect an electrical, physical, chemical, or biological property associated with the patient, and operable to convert the detected property into an electric signal;
    converting the electric signal from the at least one sensor into digital data;
    wirelessly transmitting the digital data from a patient transmitter to an evaluator station located remotely from the patient; and receiving formatting data from the evaluator station at a patient receiver, wherein the formatting data changes a format for transmission of the digital data from the patient transmitter to the evaluator station, wherein the change in the format for transmission of the digital data changes data redundancy.

2. The method of monitoring body functions of a patient according to claim 1 wherein converting, wirelessly transmitting and receiving are accomplished in one semiconductor chip.

3. The method of monitoring body functions of a patient according to claim 1 wherein the sensor is configured to be utilized with a portion of a body of the patient.

4. The method of monitoring body functions of a patient according to claim 1 wherein the sensor is adapted to be positioned in contact with a finger of the patient.

5. The method of monitoring body functions of a patient according to claim 1 wherein the sensor is located in a fingerclip.

6. The method of monitoring body functions of a patient according to claim 1 wherein the converting is performed by a converter and the sensor, the converter, the patient transmitter, and the patient receiver are configured to be utilized with a body of the patient.

7. The method of monitoring body functions of a patient according to claim 1 wherein the converting, wirelessly transmitting and receiving are accomplished in a bracelet.

8. The method of monitoring body functions of a patient according to claim 1 wherein the sensor is adapted to be placed on a wrist of the patient and wherein the body functions include oxygen saturation.

9. The method of monitoring body functions of a patient according to claim 1 wherein the converting, wirelessly transmitting and receiving are accomplished on a garment.

10. The method of monitoring body functions of a patient according to claim 1 wherein the converting, wirelessly transmitting and receiving are accomplished on a mattress.

11. The method of monitoring body functions of a patient according to claim 1 wherein the body function monitored is oxygen saturation.

12. The method of monitoring body functions of a patient according to claim 1 wherein the body function monitored is the patient's pulse.

13. The method of monitoring body functions of a patient according to claim 1 wherein the formatting data received by the patient receiver changes channel coding of the digital data.

14. The method of monitoring body functions of a patient according to claim 13 wherein the channel coding comprises a deterministic code.

15. The method of monitoring body functions of a patient according to claim 13 wherein the channel coding comprises stochastic code.

16. The method of monitoring body functions of a patient according to claim 1 wherein the evaluator station performs forward error correction.

17. The method of monitoring body functions of a patient according to claim 1 further comprising correction of errors in the formatting data received by the patient receiver.

18. The method of monitoring body functions of a patient according to claim 1 further comprising transmission of formatting data from the evaluator station to a second patient receiver.

19. The method of monitoring body functions of a patient according to claim 18 wherein the evaluator station transmits formatting data to a second patient receiver on a different patient.

20. The method of claim 19 wherein the evaluator station communicates with more than one patient receiver.

21. The method of monitoring body functions of a patient according to claim 1 further comprising the step of transmitting data from a second patient using a second patient transmitter.

22. The method of monitoring body functions of a patient according to claim 1 wherein a second patient transmitter transmits data from a second patient.

23. The method of monitoring body functions of a patient according to claim 1 in which the at least one sensor is in contact with a body of the patient and another sensor is in contact with a second body.

24. The method of monitoring body functions of a patient according to claim 1 wherein the evaluator station performs error correction on the digital data transmitted by the patient transmitter.

25. The method of monitoring body functions of a patient according to claim 1 wherein the patient transmitter responds to the received formatting data and manipulates the digital data prior to transmission.

26. The method of monitoring body functions of a patient according to claim 1 wherein the patient transmitter responds to the received formatting data and controls the digital data prior to transmission.

27. The method of monitoring body functions of a patient according to claim 1 further comprising transmitting a signal from the evaluator station to an alarm unit when the sensor is not properly fastened to a surface of a skin of the patient.

28. The method of monitoring body functions of a patient according to claim 1 wherein the digital data transmitted by the patient transmitter represents the electrical signal.

29. The method of monitoring body functions of a patient according to claim 1 wherein the digital data transmitted by the patient transmitter represents processed information.

30. The method of monitoring body functions of a patient according to claim 1 wherein the at least one sensor collects data selected from the group consisting of: respiration rate, heart rate, body temperature, perspiration, EEG signals, EKG signals, pulse oximeter signals, electrodermal activity, patient position, patient motion, and combinations thereof.

31. A method for monitoring body functions of a patient comprising:

utilizing at least one sensor with the patient, the sensor configured to detect an electrical, physical, chemical, or biological property associated with the patient, and operable to convert the detected property into an electric signal;

converting the electric signal generated by the sensor into digital data;

wirelessly transmitting the digital data from a patient transmitter to an evaluator station located remotely from the patient; and receiving formatting data from the evaluator station, wherein the formatting data changes the format of the digital data transmission from the patient transmitter to the evaluator station, wherein the change in the format of the digital data transmission changes data redundancy.

32. The method for monitoring body functions of a patient according to claim 31 further comprising:

utilizing with a second patient a sensor operable to detect an electrical, physical, chemical, or biological property associated with the second patient, and operable to convert the detected property into an electric signal;

converting the electric signal generated by the sensor utilized with the second patient into digital data;

wirelessly transmitting the digital data to the evaluator station located remotely from the second patient; and changing the format of the digital data transmission from the second patient by the evaluator station.

33. The method for monitoring body functions of a patient according to claim 31 wherein the formatting data changes the channel coding of the digital data.

34. The method for monitoring body functions of a patient according to claim 33 wherein the evaluator station performs direct error correction as a function of the channel coding.

35. The method for monitoring body functions of a patient according to claim 31 wherein the patient transmitter wirelessly transmits the digital data with channel coding.

36. The method for monitoring body functions of a patient according to claim 35 wherein the formatting data changes the channel coding of the digital data.

37. The method for monitoring body functions of a patient according to claim 31 wherein the evaluator station controls the digital data.

38. The method for monitoring body functions of a patient according to claim 31 wherein the converting and wirelessly transmitting the digital data are accomplished in a bracelet.

39. The method for monitoring body functions of a patient according to claim 31 wherein the sensor is adapted to be positioned on a wrist of the patient.

40. The method for monitoring body functions of a patient according to claim 33 wherein the body function measured is oxygen saturation.

41. The method for monitoring body functions of a patient according to claim 31 wherein the evaluator station sounds an alarm.

42. The method for monitoring body functions of a patient according to claim 31 wherein the evaluator station displays the digital data.

43. The method for monitoring body functions of a patient according to claim 31 wherein the sensor collects data selected from the group consisting of: respiration rate, heart rate, body temperature, perspiration, EEG signals, EKG signals, pulse oximeter signals, electrodermal activity, patient position, patient motion, and combinations thereof.

* * * * *